(12) United States Patent
Ie et al.

(10) Patent No.: US 8,158,275 B2
(45) Date of Patent: Apr. 17, 2012

(54) FLUORINE-CONTAINING COMPOUND AND METHOD FOR PRODUCING SAME, FLUORINE-CONTAINING POLYMER, ORGANIC THIN FILM, AND ORGANIC THIN FILM DEVICE

(75) Inventors: Yutaka Ie, Suita (JP); Yoshio Aso, Suita (JP); Masashi Nitani, Suita (JP); Masato Ueda, Tsukuba (JP)

(73) Assignees: Osaka University, Osaka (JP); Sumitomo Chemical Company, Limited, Tokyo (JP)

( * ) Notice: Subject to any disclaimer, the term of this patent is extended or adjusted under 35 U.S.C. 154(b) by 109 days.

(21) Appl. No.: 12/280,257

(22) PCT Filed: Feb. 22, 2007

(86) PCT No.: PCT/JP2007/053281
§ 371 (c)(1),
(2), (4) Date: Sep. 16, 2008

(87) PCT Pub. No.: WO2007/097395
PCT Pub. Date: Aug. 30, 2007

(65) Prior Publication Data
US 2009/0240014 A1  Sep. 24, 2009

(30) Foreign Application Priority Data

Feb. 22, 2006 (JP) .................................. 2006-045768
Oct. 5, 2006 (JP) .................................. 2006-274250

(51) Int. Cl.
*B32B 9/04* (2006.01)
(52) U.S. Cl. ........ 428/704; 528/377; 528/380; 528/401; 528/402; 528/403; 528/417; 528/423; 528/425; 570/126; 570/140; 570/141; 570/142; 548/427; 548/430; 546/10; 549/43; 549/44; 257/40
(58) Field of Classification Search .................. 528/377, 528/380, 397, 401, 402, 403, 417, 423, 425; 570/130, 140, 141, 142; 548/427, 430; 546/10; 549/31, 43, 44
See application file for complete search history.

(56) References Cited

U.S. PATENT DOCUMENTS
6,835,468 B2 * 12/2004 Cho et al. .................... 428/690
(Continued)

FOREIGN PATENT DOCUMENTS
DE   19720289 A1 * 11/1998
(Continued)

OTHER PUBLICATIONS
Macine translation of DE 19720289 A1.*
(Continued)

*Primary Examiner* — Mark Eashoo
*Assistant Examiner* — Nicole M Buie-Hatcher
(74) *Attorney, Agent, or Firm* — Sughrue Mion, PLLC

(57) ABSTRACT

Fluorinated compounds of the invention are represented by the following general formula (I):

(Chemical Formula 1)

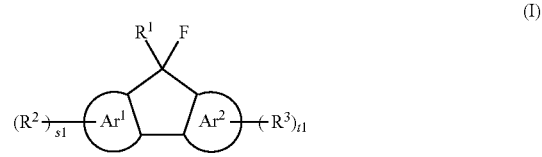

(in formula (I), $Ar^1$ and $Ar^2$ each independently represent a $C_{10}$ or greater aromatic hydrocarbon or $C_4$ or greater heterocyclic group, $R^1$ represents hydrogen or a monovalent substituent, $R^2$ and $R^3$ each independently represent a monovalent substituent, and s1 and t1 each independently represent an integer of 0 or greater. When s1 is 2 or greater, the multiple $R^2$ groups may be the same or different, and when t1 is 2 or greater the multiple $R^3$ groups may be the same or different.)

17 Claims, 14 Drawing Sheets
(1 of 14 Drawing Sheet(s) Filed in Color)

U.S. PATENT DOCUMENTS

| | | | |
|---|---|---|---|
| 2004/0106798 A1* | 6/2004 | Bremer et al. | 544/294 |
| 2004/0183068 A1 | 9/2004 | Ong et al. | |
| 2004/0186266 A1 | 9/2004 | Jiang et al. | |
| 2006/0006364 A1* | 1/2006 | Shundo et al. | 252/299.62 |
| 2006/0237695 A1* | 10/2006 | Williams et al. | 252/500 |

FOREIGN PATENT DOCUMENTS

| | | |
|---|---|---|
| EP | 1 279 689 A2 | 1/2003 |
| JP | 63148268 A | 6/1988 |
| JP | 2002-322173 A | 11/2002 |
| JP | 2003-176338 A | 6/2003 |
| JP | 2003-221579 A | 8/2003 |
| JP | 2004-339516 A | 12/2004 |
| JP | 2005-235923 A | 9/2005 |
| WO | 03/010778 A1 | 2/2003 |

OTHER PUBLICATIONS

P. Coppo, et al. "New routes to poly(4,4-dialkylcyclopentadithiophene-2,6-diyls)", J. Mater. Chem., (2002), 12, (9), pp. 2597-2599.

Coppo, P. et al., Synthesis, solid state structure and polymerisation of a fully planar cyclopentadithiophene, Chem. Commun. (Camb), 2003, No. 20, pp. 2548-2549.

Zotti, Gianni et al., Electrochemical Synthesis of Polypyrrole within Poly (4-butanesulfonate-cyclopentadithiophene), Films. A 1 : 1 Polypyrrole-Polythiophene Composite, Chemistry of Materials, 1998, 10 (2), pp. 480-485.

Masashi Nitani, et al., "A Synthesis and Properties of Oligomers Containing Fluoroalkyl-bridged Bithiophene", The Institute of Scientific and Industrial Research, Osaka University, The Chemical Society of Japan, Mar. 13, 2006.

Timothy B. Patrick, et al., "Geminal Fluorination of Diazo Compounds", J. Org. Chem, 46, American Chemical Society, 1981, pp. 3917-3920.

Chentao York, et al., "Desulfurative Fluorination Using Nitrosonium Tetrafluoroborate and Pyridinium Poly(Hydrogen Fluoride)", Tetrahedron, vol. 52, No. 1, 1996, pp. 9-14.

V. M. Karpov, et al., "Synthesis and Molecular and Crystalline Structure of Polyfluoro-1,3-Diazafluorenes", Russian Journal of Organic Chemistry, vol. 40, No. 3, 2004 (Translated from Zhurnal Organicheskoi Khimii, vol. 40, No. 3, 2004, pp. 448-452, MAIK "Nauka/Interperiodica", 2004), pp. 421-425.

Yagupolskii, L.M., et al., XP-002595932, The interaction of 2,6-dimethyl-3-5-dicarboxy-4-phenylpyridine with $SF_4$ in HF solution, Journal of Fluorine Chemistry, 67, 1994, pp. 5-6, Institute of Organic Chemistry, Ukrainian Academy of Sciences, 253660 Kiev 94 (Ukraine).

* cited by examiner b-AXIAL PROJECTION DRAWING

FLUORINE-CONTAINING COMPOUND AND METHOD FOR PRODUCING SAME, FLUORINE-CONTAINING POLYMER, ORGANIC THIN FILM, AND ORGANIC THIN FILM DEVICE

TECHNICAL FIELD

The present invention relates to fluorinated compounds and to a process for their production, as well as to fluorinated polymers, an organic thin-film and an organic thin-film device.

BACKGROUND ART

Thin-films containing organic materials with electron transport or hole transport properties have potential applications in organic thin-film devices including organic thin-film transistors, organic solar cells, optical sensors, organic electroluminescent devices and the like, but because organic n-type semiconductors (that exhibit electron transport properties) are harder to obtain than organic p-type semiconductors (that exhibit hole transport properties), a great deal of research is being expended for development of organic n-type semiconductors.

Because fluoroalkyl group-introduced π-conjugated compounds have increased electron acceptability, such compounds can potentially be developed into electron transport materials such as organic n-type semiconductors. Much research has therefore been devoted in recent years to compounds obtained by introducing fluoroalkyl groups into thiophene rings, and particularly oligothiophene rings (see Patent documents 1-4).

On the other hand, development of oligothiophenes and polythiophenes having bithiophene-crosslinked structures is also being pursued with the goal of improving twist in the molecular structure (see Non-patent documents 1, 2 and Patent document 5).

(Patent document 1) U.S. Patent Application Publication No. 2004/186266

(Patent document 2) U.S. Patent Application Publication No. 2004/183068

(Patent document 3) International Patent Publication No. WO2003/010778

(Patent document 4) European Patent Application Publication No. 1279689

(Patent document 5) Japanese Unexamined Patent Publication No. 2004-339516

(Non-patent document 1) Paolo Coppo et al., J. Mat. Commun. 2002, 12(9), 2597.

(Non-patent document 2) Paolo Coppo et al., Chem. Commun. 2003, 2548.

DISCLOSURE OF THE INVENTION

Problems to be Solved by the Invention

The performance of the known materials mentioned above as organic n-type semiconductors is less than satisfactory, and organic n-type semiconductors with further improved electron transport properties are desired.

It is therefore an object of the present invention to provide novel compounds and novel polymers that can be used as organic n-type semiconductors with excellent electron transport properties. It is another object of the invention to provide organic thin-films containing the novel compounds and/or novel polymers and organic thin-film devices comprising the organic thin-films.

Means for Solving the Problems

In order to achieve the object stated above, the invention provides fluorinated compounds represented by the following general formula (I).

(Chemical Formula 1)

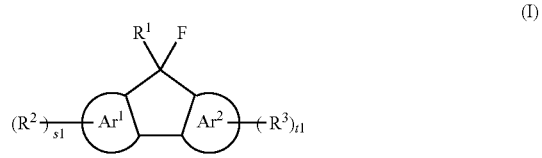

(I)

(In formula (I), $Ar^1$ and $Ar^2$ each independently represent a C10 or greater aromatic hydrocarbon or C4 or greater heterocyclic group, $R^1$ represents hydrogen or a monovalent substituent, $R^2$ and $R^3$ each independently represent a monovalent substituent, and s1 and t1 each independently represent an integer of 0 or greater. When s1 is 2 or greater, the multiple $R^2$ groups may be the same or different, and when t1 is 2 or greater the multiple $R^3$ groups may be the same or different.)

The invention further provides fluorinated polymers having a repeating unit represented by the following general formula (III).

(Chemical Formula 2)

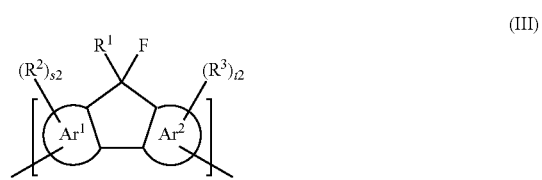

(III)

(In formula (III), $Ar^1$ and $Ar^2$ each independently represent a C10 or greater aromatic hydrocarbon or C4 or greater heterocyclic group, $R^1$ represents hydrogen or a monovalent substituent, $R^2$ and $R^3$ each independently represent a monovalent substituent, and s2 and t2 each independently represent an integer of 0 or greater. When s2 is 2 or greater, the multiple $R^2$ groups may be the same or different, and when t2 is 2 or greater the multiple $R^3$ groups may be the same or different.)

Fluorinated compounds and fluorinated polymers comprising such a backbone have a fluoroalkyl-crosslinked cyclic structure, and therefore have satisfactory π-conjugated twist between rings while exhibiting sufficiently low LUMO due to introduction of fluorine atoms, and can thus be used as organic n-type semiconductors with excellent electron transport properties. Such fluorinated compounds and fluorinated polymers are also chemically stable and have excellent solubility in solvents, and can therefore be used to form thin films to allow production of organic thin-film devices with excellent performance.

The invention further provides a process for production of fluorinated compounds according to the invention, the process comprising a step of reacting a compound represented by the following general formula (VII) with a fluoride ion source in the presence of a halonium ion generator.

(Chemical Formula 3)

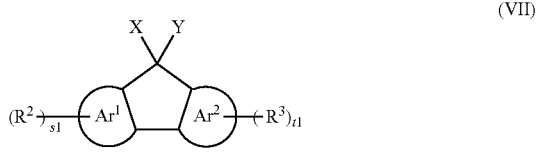

(VII)

(In formula (VII), $Ar^1$ and $Ar^2$ each independently represent a C10 or greater aromatic hydrocarbon or C4 or greater heterocyclic group, $R^2$ and $R^3$ each independently represent a monovalent substituent, X and Y each independently represent an alkylthio group, or the alkyl portions of the alkylthio groups X and Y are linked to form an alkylenedithio group, or X and Y together represent a thiocarbonyl group formed with the carbon atoms to which they are bonded, and s1 and t1 each independently represent an integer of 0 or greater. When s1 is 2 or greater, the multiple $R^2$ groups may be the same or different, and when t1 is 2 or greater the multiple $R^3$ groups may be the same or different.)

According to this process for production of fluorinated compounds, it is possible to efficiently and reliably produce fluorinated compounds of the invention as described above.

The invention still further provides an organic thin-film comprising a fluorinated compound and/or fluorinated polymer of the invention, and an organic thin-film device comprising the organic thin-film.

The organic thin-film and organic thin-film device exhibit excellent performance since they are formed using a fluorinated compound and/or fluorinated polymer according to the invention which exhibits a sufficiently low LUMO, as mentioned above.

Effect of the Invention

According to the invention it is possible to provide novel fluorinated compounds and novel fluorinated polymers that can be used as organic n-type semiconductors with excellent electron transport properties. Also according to the invention, it is possible to provide organic thin-films comprising the fluorinated compounds and/or fluorinated polymers, as well as organic thin-film devices comprising the organic thin-films.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

EXPLANATION OF SYMBOLS

Figure 1:
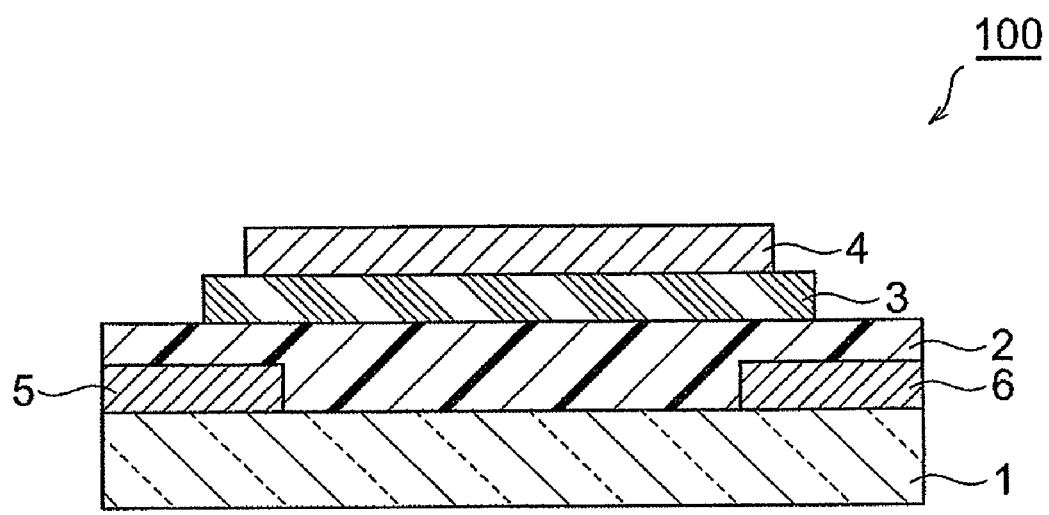
FIG. 1 is a schematic cross-sectional view of an organic thin-film transistor according to a first embodiment.

1: Substrate, 2: active layer, 2a: active layer, 3: insulating film, 4: gate electrode, 5: source electrode, 6: drain electrode, 7a: first electrode, 7b: second electrode, 8: charge generation layer, 100: first embodiment of organic thin-film transistor, 110: second embodiment of organic thin-film transistor, 120: third embodiment of organic thin-film transistor, 130: fourth embodiment of organic thin-film transistor, 140: fifth embodiment of organic thin-film transistor, 150: sixth embodiment of organic thin-film transistor, 160: seventh embodiment of organic thin-film transistor, 200: embodiment of solar cell, 300: first embodiment of optical sensor, 310: second embodiment of optical sensor, 320: third embodiment of optical sensor.

BEST MODE FOR CARRYING OUT THE INVENTION

Preferred embodiments of the invention will now be explained in detail, with reference to the accompanying drawings as necessary. Identical elements in the drawings will be referred to by like reference numerals and will be explained only once. The vertical and horizontal positional relationships are based on the positional relationships in the drawings, unless otherwise specified. Also, the dimensional proportions depicted in the drawings are not necessarily limitative.

The fluorinated compounds of the invention have a structure represented by the following general formula (I).

(Chemical Formula 4)

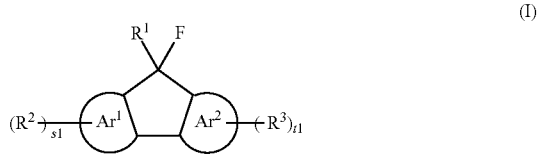

(I)

(In formula (I), $Ar^1$ and $Ar^2$ each independently represent a C10 or greater aromatic hydrocarbon or C4 or greater heterocyclic group, Ri represents hydrogen or a monovalent substituent, $R^2$ and $R^3$ each independently represent a monovalent substituent, and s1 and t1 each independently represent an integer of 0 or greater. When s1 is 2 or greater, the multiple $R^2$ groups may be the same or different, and when t1 is 2 or greater the multiple $R^3$ groups may be the same or different.)

In general formula (I), $Ar^1$ and $Ar^2$ each independently represent a C10 or greater aromatic hydrocarbon or C4 or greater heterocyclic group, which may be substituted with one or more arbitrary substituents. Also, s1 and t1 each independently represent an integer of 0 or greater, the upper limit being the number of hydrogens minus 2 that can be substituted from the C10 or greater aromatic hydrocarbon or C4 or greater heterocyclic groups represented by $Ar^1$ and $Ar^2$. Also, although $Ar^1$ and $Ar^2$ may be the same or different, $Ar^1$ and $Ar^2$ are preferably the same in order to facilitate production.

The compound represented by general formula (I) above is preferably a compound represented by the following general formula (II).

(Chemical Formula 5)

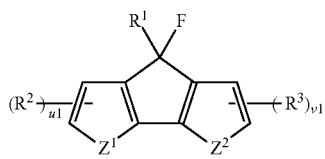

(II)

(In formula (II), $R^1$ represents hydrogen or a monovalent substituent, $R^2$ and $R^3$ each independently represent a monovalent substituent, $Z^1$ and $Z^2$ each independently represent any group represented by the following formulas (i)-(viii), and u1 and v1 each independently represent an integer of 0-2. When u1 is 2, the multiple $R^2$ groups may be the same or different, and when v1 is 2 the multiple $R^3$ groups may be the same or different. $R^4$ and $R^5$ each independently represent hydrogen or a monovalent substituent. The group represented by the following formula (viii) may be left-right inverted.)

(Chemical Formula 6)

 (i)

 (ii)

 (iii)

 (iv)

 (v)

 (vi)

 (vii)

 (viii)

A fluorinated polymer of the invention has a repeating unit represented by the following general formula (III).

(Chemical Formula 7)

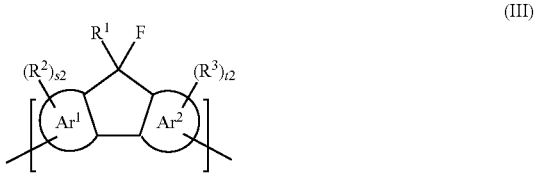

(III)

(In formula (III), $Ar^1$ and $Ar^2$ each independently represent a C10 or greater aromatic hydrocarbon or C4 or greater heterocyclic group, $R^1$ represents hydrogen or a monovalent substituent, $R^2$ and $R^3$ each independently represent a monovalent substituent, and s2 and t2 each independently represent an integer of 0 or greater. When s2 is 2 or greater, the multiple $R^2$ groups may be the same or different, and when t2 is 2 or greater the multiple $R^3$ groups may be the same or different.)

That is, a fluorinated polymer of the invention has at least one and preferably 2 or more repeating units represented by general formula (III) above, and may additionally have another repeating unit, Multiple $R^1$ groups in the polymer may be the same or different. In order to facilitate production, however, the multiple $R^1$ groups are preferably the same.

In general formula (III), $Ar^1$ and $Ar^2$ each independently represent a C10 or greater aromatic hydrocarbon or C4 or greater heterocyclic group, which may be substituted with one or more arbitrary substituents. Also, s2 and t2 each independently represent an integer of 0 or greater, the upper limit being the number of hydrogens minus 3 that can be substituted from the C10 or greater aromatic hydrocarbon or C4 or greater heterocyclic groups represented by $Ar^1$ and $Ar^2$. Also, although $Ar^1$ and $Ar^2$ may be the same or different, $Ar^1$ and $Ar^2$ are preferably the same in order to facilitate production.

The repeating unit represented by general formula (III) above is preferably a repeating unit represented by the following general formula (IV).

(Chemical Formula 8)

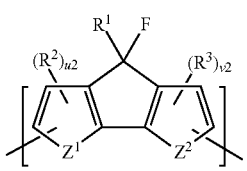

(IV)

(In formula (IV), $R^1$ represents hydrogen or a monovalent substituent, $R^2$ and $R^3$ each independently represent a monovalent substituent, $Z^1$ and $Z^2$ each independently represent any group represented by the following formulas (i)-(viii), and u2 and v2 each independently represent an integer of 0 or 1. $R^4$ and $R^5$ each independently represent hydrogen or a monovalent substituent. Also, the group represented by the following formula (viii) may be left-right inverted.)

(Chemical Formula 9)

 (i)

 (ii)

 (iii)

 (iv)

 (v)

 (vi)

 (vii)

 (viii)

A polymer of the invention may have in the molecule any one repeating unit from among the repeating units represented by general formula (III) or general formula (IV) above, or it may have more than one different repeating units. In order to facilitate production, it preferably has anyone of the repeating units.

The polymer of the invention preferably comprises at least one repeating unit represented by general formula (III) above and at least one repeating unit represented by the following general formula (V). The polymer of the invention more preferably has at least one repeating unit represented by general formula (IV) above and at least one repeating unit represented by the following general formula (V), and even more preferably at least one repeating unit represented by general formula (IV) above and at least one repeating unit represented by the following general formula (VI). Such a structure will widen the range of variability for the soluble, mechanical, thermal and electronic characteristics. In the following general formula (V), $Ar^3$ represents a divalent aromatic hydrocarbon or divalent heterocyclic group (which may be optionally substituted). About the polymer of the invention the ratio of the repeating unit represented by general formula (III) (preferably a repeating unit represented by general formula (IV) above) and the repeating unit represented by the following general formula (V) (preferably a repeating unit represented by the following general formula (VI)) is preferably 10-1000 mol of the latter to 100 mol of the former, more preferably 25-400 mol of the latter to 100 mol of the former and even more preferably 50-200 mol of the latter to 100 mol of the former.

(Chemical Formula 10)

 (V)

In this case, $Ar^3$ is preferably a group represented by the following general formula (VI). In general formula (VI), $Z^3$ may be the same as or different from $Z^1$ or $Z^2$ in general formula (IV) above, and it is a group represented by any of the following formulas (i)-(ix). In general formula (VI) below, $R^6$ and $R^7$ each independently represent hydrogen or a monovalent substituent, and $R^6$ and $R^7$ may bond together to form a ring. In the following formulas (i)-(ix), $R^4$, $R^5$, $R^8$ and $R^9$ each independently represent hydrogen or a monovalent substituent, and $R^8$ and $R^9$ may bond together to form a ring. The group represented by the following formula (viii) may be left-right inverted.

(Chemical Formula 11)

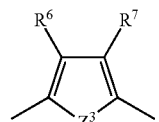 (VI)

(Chemical Formula 12)

 (i)

 (ii)

 (iii)

 (iv)

 (v)

 (vi)

 (vii)

 (viii)

(ix)

In general formulas (I) and (III) above, the C10 or greater aromatic hydrocarbon groups represented by $Ar^1$ and $Ar^2$ are atomic groups left after removing at least two hydrogen atoms from a C10 or greater fused ring, and they will generally have 10-60 and preferably 10-20 carbon atoms. As examples of fused rings there may be mentioned naphthalene, anthracene, pyrene, perylene and fluorene. The aromatic hydrocarbon groups may be optionally substituted. The numbers of carbon atoms of the substituents are not included in the number of carbon atoms in the aromatic hydrocarbon groups. As substituents there may be mentioned halogen atoms and saturated or unsaturated hydrocarbon, aryl, alkoxy, aryloxy, heterocyclic, amino, nitro and cyano groups.

In general formulas (I) and (III) above, C4 or greater aromatic heterocyclic groups represented by $Ar^1$ and $Ar^2$ are atomic groups left after removing at least two hydrogen atoms from a heterocyclic compound, and they will generally have 4-60 and preferably 4-20 carbon atoms. The heterocyclic groups may have substituents, in which case the numbers of carbon atoms of the substituents are not included in the numbers of carbon atoms of the heterocyclic groups. As substituents there may be mentioned halogen atoms and saturated or unsaturated hydrocarbon, aryl, alkoxy, aryloxy, heterocyclic, amino, nitro and cyano groups.

In general formula (V) above, the divalent aromatic hydrocarbon group represented by $Ar^3$ is an atomic group left after removing two hydrogen atoms from a benzene ring or fused ring, and it will generally have 6-60 and preferably 6-20 carbon atoms. As examples of fused rings there may be mentioned naphthalene, anthracene, pyrene, perylene and fluorene. Preferred among these are atomic groups remaining after removing two hydrogen atoms from a benzene ring or fluorene. The aromatic hydrocarbon groups may be optionally substituted. The numbers of carbon atoms of the substituents are not included in the number of carbon atoms in the divalent aromatic hydrocarbon groups. As substituents there may be mentioned halogen atoms and saturated or unsaturated hydrocarbon, aryl, alkoxy, aryloxy, heterocyclic, amino, nitro and cyano groups.

In general formula (V) above, the divalent heterocyclic group represented by $Ar^3$ may also be an atomic group remaining after removing two hydrogen atoms from a heterocyclic compound, and the number of carbon atoms will normally be 4-60 and preferably 4-20. The heterocyclic groups may have substituents, in which case the numbers of carbon atoms of the substituents are not included in the numbers of carbon atoms of the heterocyclic groups. As substituents there may be mentioned halogen atoms and saturated or unsaturated hydrocarbon, aryl, alkoxy, aryloxy, heterocyclic, amino, nitro and cyano heterocyclic ring, saturated or unsaturated, and with or without substituents), or an electron-donating or electron-withdrawing group preferably.

In addition, $R^1$-$R^9$ each independently represent hydrogen (with the proviso that both $R^2$ and $R^3$ are not simultaneously hydrogen), a halogen atom, a straight-chain or branched low molecular chain, a monovalent cyclic group with 3-60 annular atoms (which may be a monocycle or fused ring, a carbon ring or heterocyclic ring, saturated or unsaturated, and with or without substituents), a saturated or unsaturated hydrocarbon group, hydroxyl, alkoxy, alkanoyloxy, amino, oxyamino, alkylamino, dialkylamino, alkanoylamino, cyano, nitro, sulfo, alkyl substituted with one or more halogens, alkoxysulfonyl (where the alkyl group is optionally substituted with one or more halogen atoms), alkylsulfonyl (where the alkyl group is optionally substituted with one or more halogen atoms), sulfamoyl, alkylsulfamoyl, carboxyl, carbamoyl, alkylcarbamoyl, alkanoyl or alkoxycarbonyl.

According to the invention, halogen atoms include fluorine, chlorine, bromine and iodine atoms.

There are no particular restrictions on the alkyl groups, for which methyl, ethyl, n-propyl, isopropyl, n-butyl, isobutyl, sec-butyl and tert-butyl may be mentioned as examples, and this also applies for groups containing alkyl groups in their structures (such as alkoxy, alkylamino group and alkoxycarbonyl).

There are also no particular restrictions on unsaturated hydrocarbon groups, and as examples there may be mentioned vinyl, 1-propenyl, allyl, propargyl, isopropenyl, 1-butenyl and 2-butenyl. groups.

A heterocyclic compound referred to here is an organic compound with a ring structure wherein the elements composing the ring include not only carbon but also heteroatoms such as oxygen, sulfur, nitrogen, phosphorus, boron, silicon, selenium and tellurium.

In general formulas (II) and (IV), $Z^1$ and $Z^2$ each independently represent any group from among formulas (i)-(viii) above, preferably any group from among (i), (ii), (iii) and (viii), more preferably any group from among (i), (ii) and (iii) and most preferably a group represented by (i). In general formula (VI), $Z^3$ represents any group from among formulas (i)-(ix) above, preferably any group from among (i), (ii), (iii), (viii) and (ix), more preferably any group from among (i), (ii) and (iii) and most preferably a group represented by (i). Thiophene rings, furan rings and pyrrole rings, and especially thiophene rings, exhibit characteristic electrical properties, and crosslinking of two thiophene rings with fluoroalkyl can result in new electrical properties that are non-existent in the prior art.

In formulas (iii), (viii) and (ix) above, as well as general formulas (I), (II), (III), (IV) and (VI), $R^1$ and $R^4$-$R^9$ each independently represent hydrogen or an arbitrary monovalent substituent, and $R^2$ and $R^3$ each independently represent an arbitrary monovalent substituent. Also, a ring may be formed between $R^6$ and $R^7$ and between $R^8$ and $R^9$. $R^1$-$R^9$ each independently represent hydrogen (with the proviso that both $R^2$ and $R^3$ are not simultaneously hydrogen), a halogen atom, a straight-chain or branched low molecular chain, a monovalent cyclic group (which may be a monocycle or fused ring, a carbon ring or There are no particular restrictions on alkanoyl groups, for which formyl, acetyl, propionyl, isobutyryl, valeryl and isovaleryl may be mentioned as examples, and this also applies for groups containing alkanoyl groups in their structures (such as alkanoyloxy and alkanoylamino). A "C1 alkanoyl group" is formyl, and this also applies for groups containing alkanoyl groups in their structures.

More preferably, $R^1$-$R^9$ each independently represent hydrogen (with the proviso that both $R^2$ and $R^3$ are not simultaneously hydrogen), a halogen atom, or an optionally substituted saturated or unsaturated straight-chain or branched hydrocarbon, hydroxy, C1-18 straight-chain or branched alkyl, C2-18 straight-chain or branched unsaturated hydrocarbon, C1-18 straight-chain or branched alkoxy, C2-18 straight-chain or branched alkanoyloxy, amino, oxyamino, C1-18 straight-chain or branched alkylamino, dialkylamino (where the alkyl groups are C1-18 straight-chain or branched alkyl groups), C1-18 straight-chain or branched alkanoylamino, cyano, nitro, sulfo, C1-18 straight-chain or branched alkyl substituted with one or more halogen atoms, C1-18 straight-chain or branched alkoxysulfonyl (where the alkyl group is optionally substituted with one or more halogen atoms), C1-18 straight-chain or branched alkylsulfonyl (where the alkyl group is optionally substituted with one or more halogen atoms), sulfamoyl, C1-18 straight-chain or branched alkylsulfamoyl, carboxyl, carbamoyl, C1-18 straight-chain or branched alkylcarbamoyl, C1-18 straight-chain or branched alkanoyl or C1-18 straight-chain or branched alkoxycarbonyl group.

Particularly preferably, $R^1$-$R^9$ each independently represent hydrogen (with the proviso that both $R^2$ and $R^3$ are not simultaneously hydrogen), a halogen atom, or an optionally substituted saturated or unsaturated straight-chain or branched hydrocarbon chain, hydroxy, C1-6 straight-chain or branched alkyl, C2-6 straight-chain or branched unsaturated hydrocarbon, C1-6 straight-chain or branched alkoxy, C2-6 straight-chain or branched alkanoyloxy, amino, oxyamino, C1-6 straight-chain or branched alkylamino, dialkylamino (where the alkyl groups are C1-6 straight-chain or branched alkyl groups), C1-6 straight-chain or branched alkanoylamino, cyano, nitro, sulfo, C1-6 straight-chain or branched alkyl substituted with one or more halogen atoms, C1-6 straight-chain or branched alkoxysulfonyl (where the alkyl group is optionally substituted with one or more halogen atoms, C1-6 straight-chain or branched alkylsulfonyl (where the alkyl group is optionally substituted with one or more halogen atoms), sulfamoyl, C1-6 straight-chain or branched alkylsulfamoyl, carboxyl, carbamoyl, C1-6 straight-chain or branched alkylcarbamoyl, C1-6 straight-chain or branched alkanoyl or C1-6 straight-chain or branched alkoxycarbonyl group.

Most preferably, $R^1$-$R^9$ each independently represent hydrogen (with the proviso that both $R^2$ and $R^3$ are not simultaneously hydrogen), a halogen atom, a C1-18 straight-chain hydrocarbon or a monovalent cyclic group having a structure derived by removing any one hydrogen from a compound represented by any of the following formulas (1)-(67) (where the cyclic group may be further substituted with one or more substituents which are each independently selected from among halogen atoms, saturated or unsaturated hydrocarbons, aryl, alkoxy, aryloxy, heterocyclic, amino, nitro and cyano.

(Chemical Formula 13)

(1)

(2)

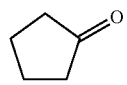
(3)

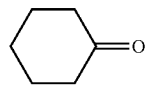
(4)

(5)

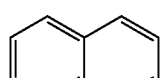
(6)

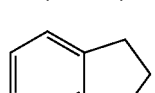
(7)

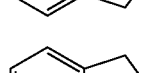
(8)

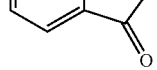
(9)

-continued

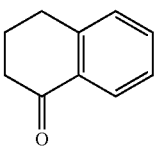
(10)

(11)

(12)

(13)

(14)

(15)

(16)

(17)

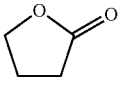
(18)

(19)

(20)

(21)

(22)

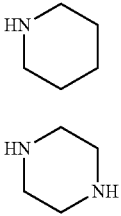
(23)

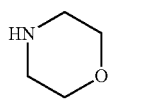 (23)
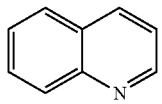 (24)
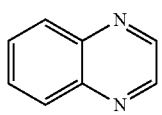 (25)
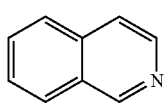 (26)
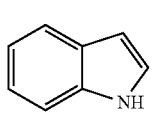 (27)
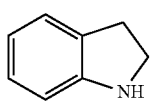 (28)
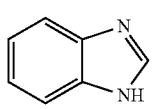 (29)
(Chemical Formula 14)
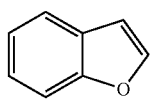 (30)
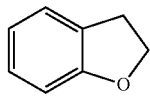 (31)
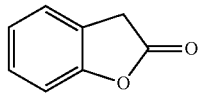 (32)
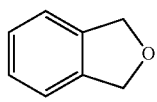 (33)
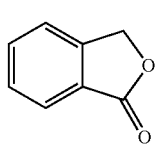 (34)
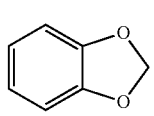 (35)
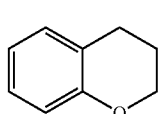 (36)
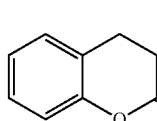 (37)
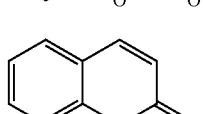 (38)
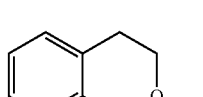 (39)
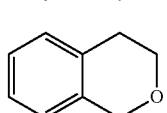 (40)
 (41)
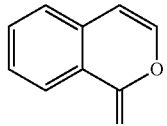 (42)
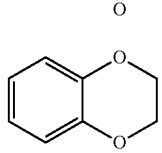 (43)

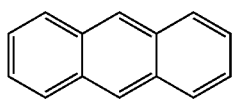

(Chemical Formula 15)

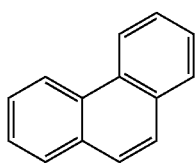

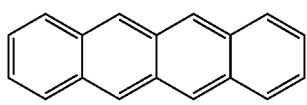

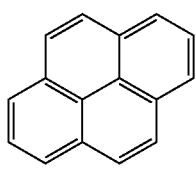

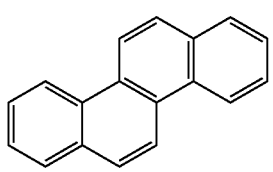

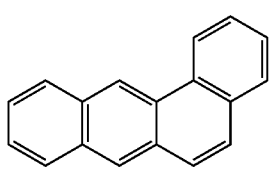

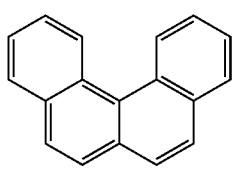

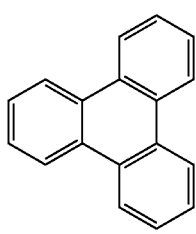

(50)
(51)
(52)
(53)
(54)
(55)
(56)
(57)
(58)
(59)
(60)
(61)

(62)
(63)
(64)
(65)
(66)
(67)

Yet more preferably, $R^2$-$R^9$ each independently represent hydroxy, or a C1-6 straight-chain or branched alkyl, C2-6 straight-chain or branched unsaturated hydrocarbon, C1-6 straight-chain or branched alkoxy, C2-6 straight-chain or branched alkanoyloxy, amino, oxyamino, C1-6 straight-chain or branched alkylamino, dialkylamino (where the alkyl groups are C1-6 straight-chain or branched alkyl groups), C1-6 straight-chain or branched alkanoylamino, cyano, nitro, sulfo, C1-6 straight-chain or branched alkyl substituted with one or more halogen atoms, C1-6 straight-chain or branched alkoxysulfonyl (where the alkyl group is optionally substituted with one or more halogen atoms), C1-6 straight-chain or branched alkylsulfonyl (where the alkyl group is substituted with one or more halogen atoms), sulfamoyl, C1-6 straight-chain or branched alkylsulfamoyl, carboxyl, carbamoyl, C1-6 straight-chain or branched alkylcarbamoyl, C1-6 straight-chain or branched alkanoyl or C1-6 straight-chain or branched alkoxycarbonyl group.

In general formulas (I), (II), (III) and (IV), $R^1$ is especially preferred to be a halogen atom and is most preferably a fluorine atom, for suitable use as an organic n-type semiconductor in the thin-film material of an organic thin-film device. A compound including a thiophene structure, or a polymer containing it, can not only lower the LUMO level by introduction of the fluorine atoms, but can also increase the solubility in organic solvents and help to improve performance as an organic semiconductor and lower production cost, since π conjugated twist is maintained due to crosslinking of thiophene rings. The organic thin-film device of the invention can exhibit high performance since it contains a compound of the invention having a fluoroalkyl-crosslinked ring structure, or a polymer containing it.

Also, a fluorinated compound according to the invention preferably has polymerizing active groups as $R^2$ and $R^3$ in general formula (I) or (II) above, thus allowing it to be used as a polymer precursor. When multiple $R^2$ groups are present in general formula (I) or (II), one of the $R^2$ groups is preferably a polymerizing active group, and when multiple $R^3$ groups are present, one of the $R^3$ groups is preferably a polymerizing group. That is, the fluorinated compound of the invention preferably has two polymerizing active groups in the molecule when it is to be used as a polymer precursor. Examples of polymerizing active groups include halogen atoms, and alkyl sulfonate, aryl sulfonate, arylalkyl sulfonate, alkylstannyl, arylstannyl, arylalkylstannyl, boric acid ester, sulfoniummethyl, phosphoniummethyl, phosphonatemethyl, monohalogenated methyl, boric acid, formyl and vinyl groups, among which halogen atoms, alkylstannyl groups and boric acid ester groups are preferred.

When a compound of the invention is to be used as an organic thin-film and polymerizing active groups remain at the ends, they may be protected with stable groups to avoid potential reduction in the characteristics and durability of devices formed therefrom.

$R^2$ and $R^3$ in general formula (I) or (II) are preferably each independently alkyl, alkoxy, fluoroalkyl, fluoroalkoxy, aryl, heterocyclic, electron-donating or electron-withdrawing groups, with fluoroalkyl, fluoroalkoxy and electron-withdrawing groups being preferred from the viewpoint of enhancing the electron transport property.

The fluorinated polymers of the invention will now be explained. A fluorinated polymer according to the invention is not particularly restricted so long as it contains a repeating unit represented by general formula (III) or (IV) above, as already mentioned, and it may optionally contain two or more of the repeating units represented by general formula (III) or (IV). It may also contain a repeating unit represented by general formula (V) or (VI) above in addition to the repeating unit represented by general formula (III) or (IV), and may even contain two or more repeating units represented by general formula (V) or (VI).

The fluorinated polymer of the invention preferably has a structure wherein a repeating unit represented by general formula (III) or (IV) is adjacent to a repeating unit represented by general formula (V) or (VI). When a repeating unit represented by general formula (III) or (IV) is adjacent to a repeating unit represented by general formula (V) or (VI), it is possible to reduce the torsional angle between the adjacent aromatic rings or heterocyclic rings, thus improving the intramolecular twist, widening the intramolecular π conjugation and lowering the LUMO level, and enhancing the electron transport property as a result. The torsional angle is defined as the angle between 0-90 degrees among the angles formed between the plane containing the aromatic ring or heterocyclic ring represented by general formula (III) or (IV) and the plane containing its adjacent bonding aromatic ring or heterocyclic ring. When a repeating unit represented by general formula (III) or (IV) is adjacent to a repeating unit represented by general formula (V) or (VI), the torsional angle will usually be 0-45 degrees, typically 0-40 degrees and even more typically 0-30 degrees.

Figure 9:
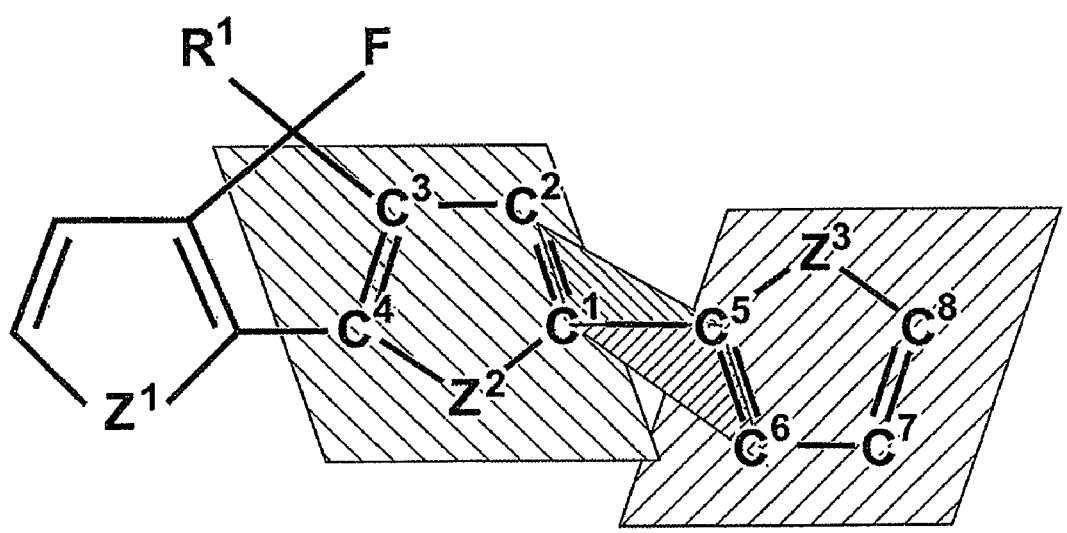
FIG. 9 is a drawing showing the torsional angle formed between the ring of the repeating unit represented by general formula (IV) and the ring of the repeating unit represented by general formula (VI).

FIG. 9 is a drawing showing the torsional angle formed between the ring of the repeating unit represented by general formula (IV) above and the ring of the repeating unit represented by general formula (VI) above. The torsional angle is the angle formed between the plane formed by $C^2$—$C^1$-$C^5$ and the plane formed by $C^1$-$C^5$—$C^6$ in FIG. 9. From the viewpoint of increasing the intramolecular twist, the sum of the number of ring structures containing $Z^1$ or $Z^2$ in the structure represented by general formula (IV) above (for example, thiophene rings when $Z^1$ or $Z^2$ is a group represented by formula (i) above), and the number of ring structures containing $Z^3$ represented by general formula (VI) above is 3 or greater, and the rings are preferably in continuous linkage, while more preferably the total number of ring structures containing $Z^1$, $Z^2$ or $Z^3$ is 4 or greater and the rings are in continuous linkage.

The fluorinated polymer of the invention is preferably represented by the following general formula (VIII), (IX) or (X) from the viewpoint of increasing the electron transport property.

(Chemical Formula 16)

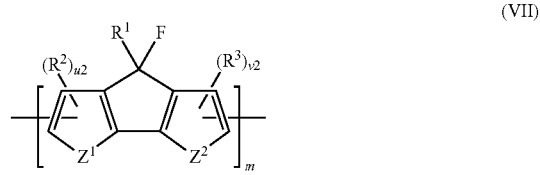

(VIII)

(Chemical Formula 17)

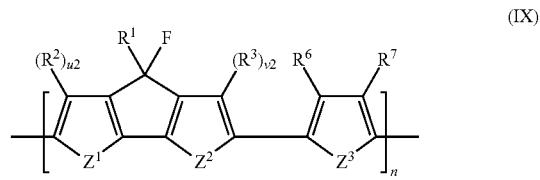

(IX)

(Chemical Formula 18)

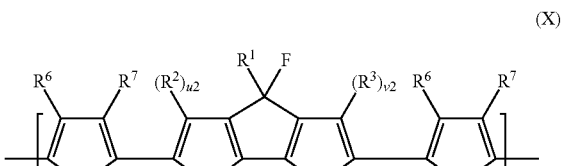

(X)

In general formulas (VIII)-(X), $Z^1$, $Z^2$, $Z^3$, $R^1$, $R^2$, $R^3$, $R^6$ and $R^7$ have the same definitions as $Z^1$, $Z^2$, $Z^3$, $R^1$, $R^2$, $R^3$, $R^6$ and $R^7$ in general formulas (I)-(IV) and (VI). When multiple $Z^1$, $Z^2$, $Z^3$, $R^1$, $R^2$, $R^3$, $R^6$ and $R^7$ groups are present they may be the same or different. The letter m represents an integer of 2-500 and preferably an integer of 3-20. The letter n represents an integer of 1-500 and preferably an integer of 2-20. The letter p represents an integer of 1-500 and preferably an integer of 1-10. Most preferably, $Z^1$, $Z^2$ and $Z^3$ are all sulfur atoms and $R^1$ is a fluorine atom.

When a polymer of the invention has polymerizing active groups as terminal groups, they may also be used as polymer precursors for another polymer. In this case, the polymer of the invention preferably has two polymerizing active groups in the molecule. Examples of polymerizing active groups include halogen atoms, and alkyl sulfonate, aryl sulfonate, arylalkyl sulfonate, alkylstannyl, arylstannyl, arylalkylstannyl, boric acid ester, sulfoniummethyl, phosphoniummethyl, phosphonatemethyl, monohalogenated methyl, boric acid, formyl and vinyl groups, among which halogen atoms, alkylstannyl groups and boric acid ester groups are preferred.

When a polymer of the invention is to be used as an organic thin-film and polymerizing active groups remain at the ends, they are preferably protected with stable groups to avoid potential reduction in the characteristics and durability of devices formed therefrom.

The terminal groups may be hydrogen, alkyl, alkoxy, fluoroalkyl, fluoroalkoxy, aryl, heterocyclic groups, electron-donating groups or electron-withdrawing groups, among which fluoroalkyl, fluoroalkoxy and electron-withdrawing groups are preferred from the viewpoint of enhancing the electron transport property. They preferably have conjugated bonds that are continuous with the conjugated structure of the main chain, and for example, the structure may include bonding with aryl or heterocyclic groups via carbon-carbon bonds.

As particularly preferred examples of fluorinated polymers of the invention there may be mentioned compounds represented by the following general formulas (68)-(72).

(Chemical Formula 19)

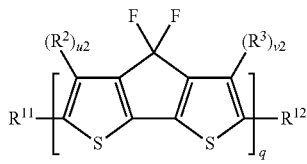

(68)

(Chemical Formula 20)

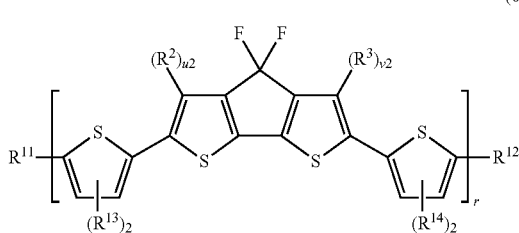

(69)

(Chemical Formula 21)

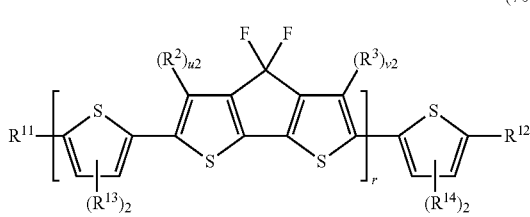

(70)

(Chemical Formula 22)

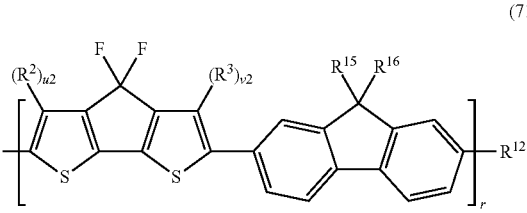

(71)

(Chemical Formula 23)

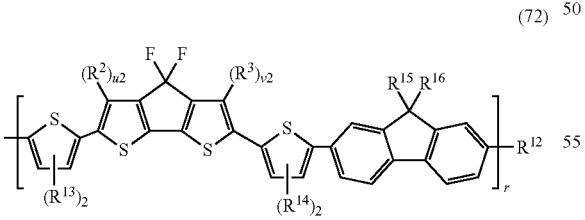

(72)

In general formulas (68)-(72), $R^{11}$ and $R^{12}$ represent terminal groups which may be the same or different, and the aforementioned terminal groups may be mentioned as examples, among which fluoroalkyl is preferred. Also, $R^{13}$, $R^{14}$, $R^{15}$ and $R^{16}$ each independently represent hydrogen or an arbitrary substituent, being preferably alkyl or alkoxy and more preferably alkyl. Multiple $R^{13}$, $R^{14}$, $R^{15}$ and $R^{16}$ groups in the polymer may be the same or different. In order to facilitate production, the multiple $R^{13}$, $R^{14}$, $R^{15}$ and $R^{16}$ groups are preferably the same. $R^2$, $R^3$, u2 and v2 have the same definitions as $R^2$, $R^3$, u2 and v2 in general formulas (I) and (IV).

Also, q and r may be selected as appropriate for the method used to form the organic thin-film with the polymer. When the organic thin-film is formed using a vapor growth process such as vacuum vapor deposition, the polymer is preferably an oligomer, q is preferably an integer of 2-10, more preferably an integer of 3-10 and even more preferably an integer of 3-5, and r is preferably an integer of 1-10, more preferably an integer of 2-10 and even more preferably an integer of 2-5. On the other hand, when the organic thin-film is formed using a method of coating a solution containing the polymer dissolved in an organic solvent, q and r are preferably integers of 3-500, more preferably integers of 6-300 and even more preferably integers of 20-200. From the viewpoint of homogeneity of the film when the film is formed by coating, the number-average molecular weight of the polymer based on polystyrene is preferably between $1 \times 10^3$ and $1 \times 10^8$ and more preferably between $1 \times 10^4$ and $1 \times 10^6$.

There are no particular restrictions on the process for production of a fluorinated compound according to the invention or a fluorinated polymer derived therefrom, and any desired process may be employed, although the production process described below is preferably used for the production.

A fluorinated compound of the invention represented by general formula (I) above may be produced by a production process comprising a fluorinating step in which a compound represented by the following general formula (VII) or a compound represented by the following general formula (VIIa) is used as the precursor and the precursor is reacted with a fluorinating agent. Specifically, a compound represented by general formula (I) may be produced by a production process comprising a step in which a compound represented by the following general formula (VIIa) is used as a precursor for reaction with a fluorinating agent, for example, in the same manner as the method of alcohol fluorination described in Organic Reactions vol. 35, p. 315 (1988) Chap. 3, "Fluorination with DAST". As an example of such a reaction step there may be mentioned the step of conversion from compound (73) to compound (74) shown below as reaction step (a).

(Chemical Formula 24)

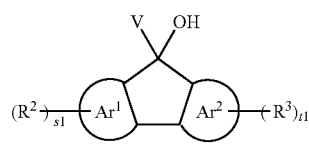

(VIIa)

(In formula (VIIa), $Ar^1$ and $Ar^2$ each independently represent a C10 or greater aromatic hydrocarbon or C4 or greater heterocyclic group, $R^2$ and $R^3$ each independently represent a monovalent substituent, V represents hydroxyl or a monovalent substituent, and s1 and t1 each independently represent an integer of 0 or greater. When s1 is 2 or greater, the multiple $R^2$ groups may be the same or different, and when t1 is 2 or greater the multiple $R^3$ groups may be the same or different.)

(Chemical Formula 25)

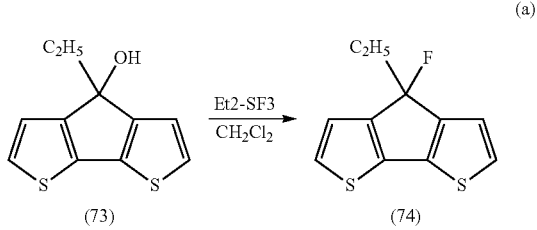

Of the compounds of the invention represented by general formula (I) above, compounds wherein $R^1$ is a fluorine atom are preferably produced by a production process comprising a step in which a compound represented by the following general formula (VII) is used as the precursor for reaction with a fluoride ion source in the presence of a halonium ion generator. As an example of such a reaction step there may be mentioned the step of conversion from compound (75) to compound (76) shown below as reaction step (b).

(Chemical Formula 26)

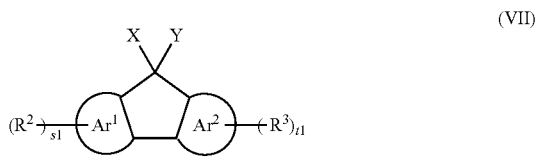

(In formula (VII), $Ar^1$ and $Ar^2$ each independently represent a C10 or greater aromatic hydrocarbon or C4 or greater heterocyclic group, $R^2$ and $R^3$ each independently represent a monovalent substituent, X and Y each independently represent an alkylthio group, or the alkyl portions of the alkylthio groups X and Y are linked to form an alkylenedithio group, or X and Y together represent a thiocarbonyl group formed with the carbon atoms to which they are bonded, and s1 and t1 each independently represent an integer of 0 or greater. When s1 is 2 or greater, the multiple $R^2$ groups may be the same or different, and when t1 is 2 or greater the multiple $R^3$ groups may be the same or different.)

(Chemical Formula 27)

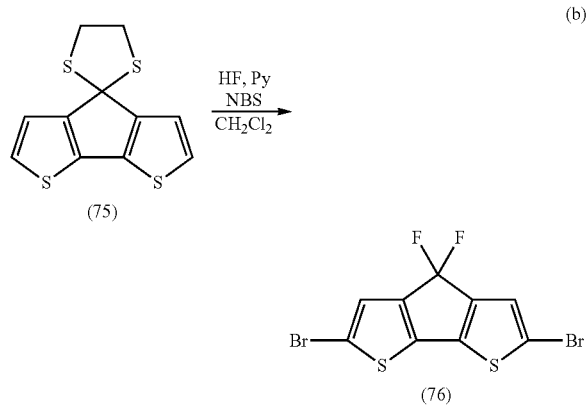

There are no particular restrictions on the reaction conditions for the reaction step described above using a compound represented by general formula (VII) as the precursor, and for example, the conditions may be appropriately selected with reference to known conversion reactions from alkylsulfanyl groups (alkylthio groups) to fluoro groups (see Japanese Unexamined Patent Publication HEI No. 6-135869, for example). This will now be explained in further detail.

First, preferred examples of fluoride ion sources include hydrogen fluoride, complexes of hydrogen fluoride and amines, complexes of hydrogen fluoride and pyridine, quaternary ammonium dihydrogen trifluorides and quaternary phosphonium dihydrogen trifluorides, any of which may be used alone or in combinations of two or more. An example of a suitable fluoride ion source is $(HF)_9$/pyridine complex.

As examples of the amines there may be mentioned nitrogen-containing cyclic compounds such as pyridine, and alkylamines such as triethylamine and diisopropylethylamine. There are no particular restrictions on quaternary ammonium dihydrogen trifluorides and quaternary phosphonium dihydrogen trifluorides, and any known compounds are suitable for use. As examples of quaternary ammonium dihydrogen trifluorides there may be mentioned compounds represented by the following general formula (XI), and as examples of quaternary phosphonium dihydrogen trifluorides there may be mentioned compounds represented by the following general formula (XII).

$$R^{20}R^{21}R^{22}R^{23}N^+H_2F_3^- \quad (XI)$$

$$R^{24}R^{25}R^{26}R^{27}P^+H_2F_3^- \quad (XII)$$

In general formulas (XI) and (XII), $R^{20}$, $R^{21}$, $R^{22}$, $R^{23}$, $R^{24}$, $R^{25}$, $R^{26}$ and $R^{27}$ each independently represent a hydrocarbon group such as alkyl, aryl or benzyl. As examples of quaternary ammonium dihydrogen trifluorides represented by general formula (XI) above there may be mentioned tetramethylammonium dihydrogen trifluoride, tetraethylammonium dihydrogen trifluoride, tetrabutylammonium dihydrogen trifluoride ($TBAH_2F_3$), benzyltrimethylammonium dihydrogen trifluoride, benzyltriethylammonium dihydrogen trifluoride and cetyltrimethylammonium dihydrogen trifluoride. These may be easily synthesized from 50% hydrofluoric acid, potassium fluoride and quaternary ammonium fluoride (for example, see Bull. Soc. Chim. Fr., 910 (1986)). As examples of quaternary phosphonium dihydrogen trifluorides represented by general formula (XII) above there may be mentioned tetramethylphosphonium dihydrogen trifluoride, tetraethylphosphonium dihydrogen trifluoride, tetrabutylphosphonium dihydrogen trifluoride, benzyltrimethylphosphonium dihydrogen trifluoride, benzyltriethylphosphonium dihydrogen trifluoride and cetyltrimethylphosphonium dihydrogen trifluoride.

The amount of fluoride ion source used in the reaction step described above is not particularly restricted, and for example, it may be from 3 equivalents to a large excess as fluoride ion, while it is preferably 3-5 equivalents, for example, from the viewpoint of reaction efficiency and cost.

There are no particular restrictions on the halonium ion generator used in the reaction step described above and any publicly known one, such as 1,3-dibromo-5,5-dimethylhydantoin (DBH), N-bromosuccinic acid imide (NBS), N-bromoacetamide (NBA), 2,4,4,6-tetrabromo-2,5-cyclohexadienone or N-iodosuccinic acid imide (NIS), may be employed. The amount of halonium ion generator used is not particularly restricted, and for example, it may be from 3 equivalents to a large excess as halonium ion, while it is preferably 3-5 equivalents, for example, from the viewpoint of reaction efficiency and cost.

A solvent may also be appropriately used as necessary in the reaction step described above. There are no particular restrictions on the solvent but it is preferably one that does not interfere with the desired reaction, and as examples there may be mentioned aliphatic hydrocarbons such as hexane, aromatic hydrocarbons such as benzene and toluene, nitrites such as acetonitrile, ethers such as diethyl ether, tetrahydrofuran and 1,2-dimethoxyethane, and halogenated solvents such as dichloromethane, 1,2-dichloroethane and carbon tetrachloride. These may be used alone or in combinations of two or more. An example of an ideal solvent is dichloromethane.

There are no particular restrictions on the reaction temperature and reaction time in the reaction step, and they may be appropriately selected according to the type of precursor. The reaction temperature may be in the range of between −100° C. and 100° C., for example.

The production process of the invention permits convenient and high yield production of cyclic compounds crosslinked with fluoroalkyl groups, and especially compounds with a difluoroalkyl-crosslinked bithiophene structure, which have not been obtainable in the prior art. In the fluorination reaction conducted in the production process of the invention, it is possible to accomplish fluorination using fluorinating reagents which are inexpensive and easily manageable.

When fluorinated compound of the invention is to be used as a material for an organic thin-film device, the produced compound is preferably subjected to purification treatment by a method such as distillation, sublimation purification or recrystallization, since the purity will affect the device characteristics.

A process for production of fluorinated compounds according to the invention was explained above, but the reaction conditions and reagents for the production process of the invention may be selected as appropriate without being limited to the examples described above. The fluorinated compounds of the invention represented by general formula (I) above are preferably produced by the production process of the invention as mentioned above, but this is not limitative and they may be produced by other processes as well.

A process for production of fluorinated polymers according to the invention will now be explained. The fluorinated polymers of the invention may be produced, for example, by a reaction wherein the starting materials are compounds represented by the following general formulas (XIII)-(XVI).

(Chemical Formula 28)

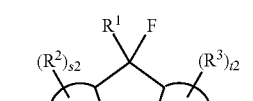

(XIII)

(Chemical Formula 29)

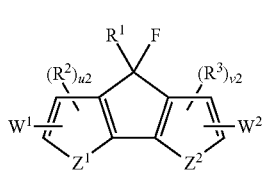

(XIV)

(Chemical Formula 30)

$W^1$—$Ar^3$—$W^2$ (XV)

(Chemical Formula 31)

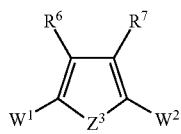

(XVI)

In general formulas (XIII)-(XVI), $Ar^1$, $Ar^2$, $Ar^3$, $Z^1$, $Z^2$, $Z^3$, $R^1$, $R^2$, $R^3$, $R^6$, $R^7$, s2, t2, u2 and v2 have the same definitions as $Ar^1$, $Ar^2$, $Ar^3$, $Z^1$, $Z^2$, $Z^3$, $R^1$, $R^2$, $R^3$, $R^6$, $R^7$, s2, t2, u2 and v2 in general formulas (I)-(VI) above. Also, $W^1$ and $W^2$ each independently represent a halogen atom or an alkyl sulfonate, aryl sulfonate, arylalkyl sulfonate, alkylstannyl, arylstannyl, arylalkylstannyl, boric acid ester, sulfoniummethyl, phosphoniummethyl, phosphonatemethyl, monohalogenated methyl, boric acid, formyl or vinyl group.

From the viewpoint of facilitating synthesis and reaction of the compounds represented by general formulas (XIII)-(XVI), $W^1$ and $W^2$ preferably each independently represent a halogen atom or an alkyl sulfonate, aryl sulfonate, arylalkyl sulfonate, alkylstannyl, boric acid ester or boric acid group.

As examples of reaction methods to be used for production of a polymer of the invention, there may be mentioned Wittig reaction methods, Heck reaction methods, Horner-Wadsworth-Emmons reaction methods, Knoevenagel reaction methods, Suzuki coupling reaction methods, Grignard reaction methods, Stille reaction methods and Ni(0) catalyst methods. The polymer may also be formed by a reaction that is not dependent on the polymerizable functional groups. For example, fused ring compounds of general formula (I) wherein s1 and t1 are zero may be subjected to repeated polymerization by oxidative polymerization using $FeCl_3$, or polymerization reaction by electrochemical oxidation.

Of the methods mentioned above, there are preferred Wittig reaction methods, Heck reaction methods, Horner-Wadsworth-Emmons reaction methods, Knoevenagel reaction methods, Suzuki coupling reaction methods, Grignard reaction methods, Stille reaction methods and Ni(0) catalyst polymerization methods, for easier structural control. Also, processes employing Suzuki coupling reaction, processes employing Grignard reaction, processes employing Stille reaction and processes employing Ni(0) catalysts are preferred for ready availability of starting materials and simplification of the reaction procedure.

The monomer (compound represented by any of general formulas (XIII)-(XVI) above) may be dissolved in an organic solvent if necessary and reacted between the melting point and boiling point of the organic solvent using an alkali or appropriate catalyst, for example.

The organic solvent used will differ depending on the compounds and reaction employed, but in order to limit secondary reactions it is generally preferred to be one that accomplishes sufficient deoxygenation treatment and promotes the reaction in an inert atmosphere. Similarly, dehydration treatment is also preferably carried out. (This does not apply, however, for reactions conducted in a two-phase system with water, such as the Suzuki coupling reaction.)

During production of a polymer according to the invention, an appropriate alkali or an appropriate catalyst may be added for reaction of the compound represented by any of general formulas (XIII)-(XVI). They may be selected as appropriate for the reaction employed. The alkali or catalyst used is preferably one that thoroughly dissolves in the solvent used for the reaction.

When a polymer of the invention is to be used as a material for an organic thin-film device, the monomer is preferably polymerized after being purified by a method such as distillation, sublimation purification or recrystallization, and after synthesis, it is preferably further subjected to purification by reprecipitating purification or chromatographic separation, since the purity will affect the device characteristics.

Examples of solvents to be used for the reaction include saturated hydrocarbons such as pentane, hexane, heptane, octane and cyclohexane, unsaturated hydrocarbons such as benzene, toluene, ethylbenzene and xylene, halogenated saturated hydrocarbons such as carbon tetrachloride, chloroform, dichloromethane, chlorobutane, bromobutane, chloropentane, bromopentane, chlorohexane, bromohexane, chlorocyclohexane and bromocyclohexane, halogenated unsaturated hydrocarbons such as chlorobenzene, dichlorobenzene and trichlorobenzene, alcohols such as methanol, ethanol, propanol, isopropanol, butanol and t-butyl alcohol, carboxylic acids such as formic acid, acetic acid and propionic acid, ethers such as dimethyl ether, diethyl ether, methyl-t-butyl ether, tetrahydrofuran, tetrahydropyran and dioxane, and inorganic acids such as hydrochloric acid, hydrobromic acid, hydrofluoric acid, sulfuric acid and nitric acid, which may be used as simple solvents or as mixed solvents.

The reaction may be followed by ordinary post-treatment such as, for example, quenching with water, subsequent extraction with an organic solvent and distillation of the solvent to obtain a product. Isolation and purification of the product can be carried out by chromatographic fractionation or recrystallization.

An organic thin-film according to the invention will now be explained. The organic thin-film of the invention is characterized by comprising a fluorinated compound and/or fluorinated polymer of the invention.

The film thickness of the organic thin-film of the invention will usually be about 1 nm-100 μm, preferably 2 nm-1000 nm, even more preferably 5 nm-500 nm and most preferably 20 nm-200 nm.

The organic thin-film may contain only one of the aforementioned compounds and polymers alone, or it may include two or more of such compounds and polymers. In order to enhance the electron transport and hole transport properties of the organic thin-film, a low molecular compound or polymer having an electron transport or hole transport property may also be combined with the compound or polymer.

Any known materials with hole transport properties may be used, examples of which include pyrazoline derivatives, arylamine derivatives, stilbene derivatives, triphenyldiamine derivatives, oligothiophenes and their derivatives, polyvinylcarbazoles and their derivatives, polysilanes and their derivatives, polysiloxane derivatives having aromatic amines on side chains or the main chain, polyanilines and their derivatives, polythiophenes and their derivatives, polypyrroles and their derivatives, polyphenylenevinylenes and their derivatives, and polythienylenevinylenes and their derivatives. Any known materials with electron transport properties may also be used, examples of which include oxadiazole derivatives, anthraquinodimethanes and their derivatives, benzoquinones and their derivatives, naphthoquinones and their derivatives, anthraquinones and their derivatives, tetracyanoanthraquinodimethanes and their derivatives, fluorenone derivatives, diphenyldicyanoethylenes and their derivatives, diphenoquinone derivatives, or metal complexes of 8-hydroxyquinolines and their derivatives, polyquinolines and their derivatives, polyquinoxalines and their derivatives, polyfluorenes and their derivatives and $C_{60}$ or other fullerenes and their derivatives.

An organic thin-film of the invention may also contain a charge generation material for generation of an electrical charge upon absorption of light in the organic thin-film. Any publicly known charge generation material may be used, and examples include azo compounds and their derivatives, diazo compounds and their derivatives, ametallic phthalocyanine compounds and their derivatives, metallic phthalocyanine compounds and their derivatives, perylene compounds and their derivatives, polycyclic quinone-based compounds and their derivatives, squarylium compounds and their derivatives, azulenium compounds and their derivatives, thiapyrylium compounds and their derivatives, and $C_{60}$ or other fullerenes and their derivatives.

The organic thin-film of the invention may also contain materials necessary for exhibiting various functions. As examples there may be mentioned sensitizing agents to enhance the function of generating electrical charge by light absorption, stabilizers to increase stability, and NV absorbers for absorption of UV light.

The organic thin-film of the invention may also contain high molecular compound materials as macromolecular binders in addition to the aforementioned compounds and polymers, in order to enhance the mechanical properties. As high molecular binders there are preferably used ones that produce minimal interference with the electron transport or hole transport property, and ones with weak absorption for visible light.

As examples of such macromolecular binders there may be mentioned poly(N-vinylcarbazole), polyanilines and their derivatives, polythiophenes and their derivatives, poly(p-phenylenevinylene) and its derivatives, poly(2,5-thienylenevinylene) and its derivatives, polycarbonates, polyacrylates, polymethyl acrylate, polymethyl methacrylate, polystyrene, polyvinyl chloride, polysiloxanes and the like.

There are no particular restrictions on the process for production of an organic thin-film of the invention, and for example, there may be employed a process of film formation using a solution comprising the compound and/or polymer and, as necessary, an electron transporting or hole transporting material and a high molecular binder in admixture therewith. A thin-film can be formed by vacuum vapor deposition when using a compound of the invention and/or an oligomer comprising it.

The solvent used for film formation from a solution is not particularly restricted so long as it dissolves the compound and/or polymer and the electron transporting or hole transporting materials and high molecular binder combined therewith as necessary. As specific examples of such solvents there may be mentioned unsaturated hydrocarbon-based solvents such as toluene, xylene, mesitylene, tetralin, decalin and n-butylbenzene, halogenated saturated hydrocarbon-based solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane, halogenated unsaturated hydrocarbon-based solvents such as chlorobenzene, dichlorobenzene and trichlorobenzene, and ether-based solvents such as tetrahydrofuran and tetrahydropyran. Dissolution in such solvents will normally be to at least 0.1 wt %, although this will differ depending on the structure and molecular weight of the compound and/or polymer.

The method of forming the film from the solution may be a coating method such as spin coating, casting, microgravure coating, gravure coating, bar coating, roll coating, wire bar coating, dip coating, spray coating, screen printing, flexographic printing, offset printing, ink jet printing, dispenser printing, nozzle coating, capillary coating or the like, among which spin coating, flexographic printing, ink jet printing, dispenser printing, nozzle coating and capillary coating method methods are preferred.

The step of producing the organic thin-film of the invention may also include a step of orienting the compound and/or polymer. An organic thin-film having the compound and/or polymer oriented by such a step will have the main chain molecules or side chain molecules aligned in a single direction, thus improving the electron mobility or hole mobility.

The method of orienting the compound and/or polymer may be a known method for orienting liquid crystals. Rubbing, photoorientation, shearing (shear stress application) and pull-up coating methods are convenient, useful and easy orienting methods, and rubbing and shearing are especially preferred among these.

Since the organic thin-film of the invention has an electron transport or hole transport property, the transport of electrons or holes introduced from the electrode or charge generated by photoabsorption can be controlled for use in various organic thin-film devices such as organic thin-film transistors, organic solar cells, optical sensors and the like. When an organic thin-film of the invention is used in such organic thin-film devices, it is preferably used after orientation by orienting treatment in order to further enhance the electron transport or hole transport properties.

Application of an organic thin-film of the invention to an organic thin-film transistor will now be explained. The organic thin-film transistor may have a structure comprising a source electrode and drain electrode, an organic thin-film layer (active layer) containing a compound and/or polymer according to the invention which acts as a current channel between them, and a gate electrode that controls the level of current flowing through the current channel, and as examples there may be mentioned organic thin-film transistors such as field-effect type or static induction type transistors.

A field-effect organic thin-film transistor may have a structure comprising a source electrode and drain electrode, an organic thin-film layer (active layer) containing a compound and/or polymer according to the invention which acts as a current channel between them, a gate electrode that controls the level of current flowing through the current channel, and an insulating layer situated between the active layer and the gate electrode. Preferably, the source electrode and drain electrode are provided in contact with the organic thin-film layer (active layer) containing the compound and/or polymer of the invention, and the gate electrode is provided sandwiching the insulating layer which is also in contact with the organic thin-film layer.

A static induction-type organic thin-film transistor has a structure comprising a source electrode and drain electrode, an organic thin-film layer containing a compound and/or polymer according to the invention which acts as a current channel between them and a gate electrode that controls the level of current flowing through the current channel, preferably with the gate electrode in the organic thin-film layer. Most preferably, the source electrode, the drain electrode and the gate electrode formed in the organic thin-film layer are provided in contact with the organic thin-film layer containing the compound and/or polymer of the invention. The structure of the gate electrode may be any one that forms a current channel for flow from the source electrode to the drain electrode, and that allows the level of current flowing through the current channel to be controlled by the voltage applied to the gate electrode; an example of such a structure is a comb-shaped electrode.

FIG. 1 is a schematic cross-sectional view of an organic thin-film transistor (field-effect organic thin-film transistor) according to a first embodiment. The organic thin-film transistor 100 shown in FIG. 1 comprises a substrate 1, a source electrode 5 and drain electrode 6 formed at a fixed spacing on the substrate 1, an active layer 2 formed on the substrate 1 covering the source electrode 5 and drain electrode 6, an insulating layer 3 formed on the active layer 2, and a gate electrode 4 formed on the insulating layer 3 covering the region of the insulating layer 3 between the source electrode 5 and drain electrode 6.

Figure 2:
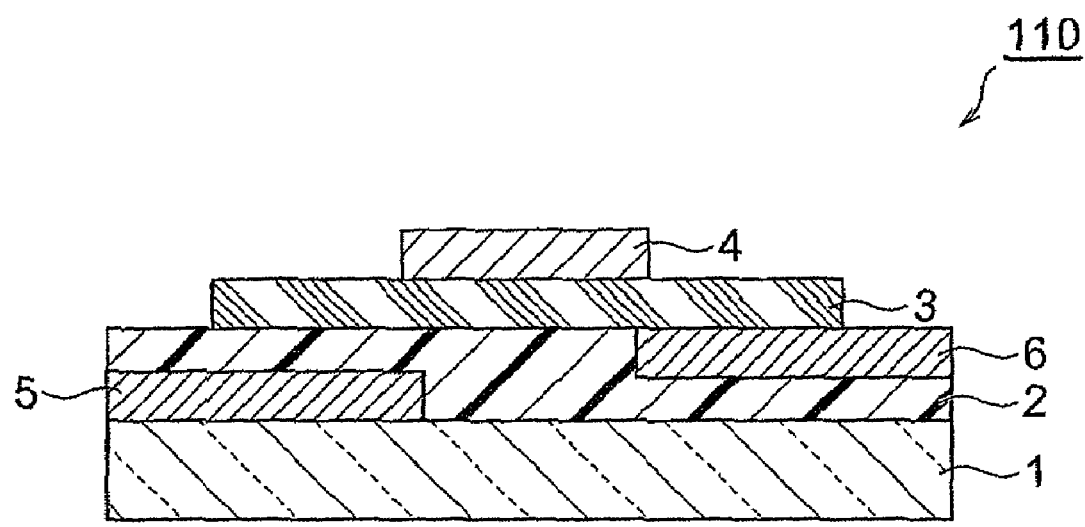
FIG. 2 is a schematic cross-sectional view of an organic thin-film transistor according to a second embodiment.

FIG. 2 is a schematic cross-sectional view of an organic thin-film transistor (field-effect organic thin-film transistor) according to a second embodiment. The organic thin-film transistor 110 shown in FIG. 2 comprises a substrate 1, a source electrode 5 formed on the substrate 1, an active layer 2 formed on the substrate 1 covering the source electrode 5, a drain electrode 6 formed on the active layer 2 at a prescribed spacing from the source electrode 5, an insulating layer 3 formed on the active layer 2 and drain electrode 6, and a gate electrode 4 formed on the insulating layer 3 covering the region of the insulating layer 3 between the source electrode 5 and drain electrode 6.

Figure 3:
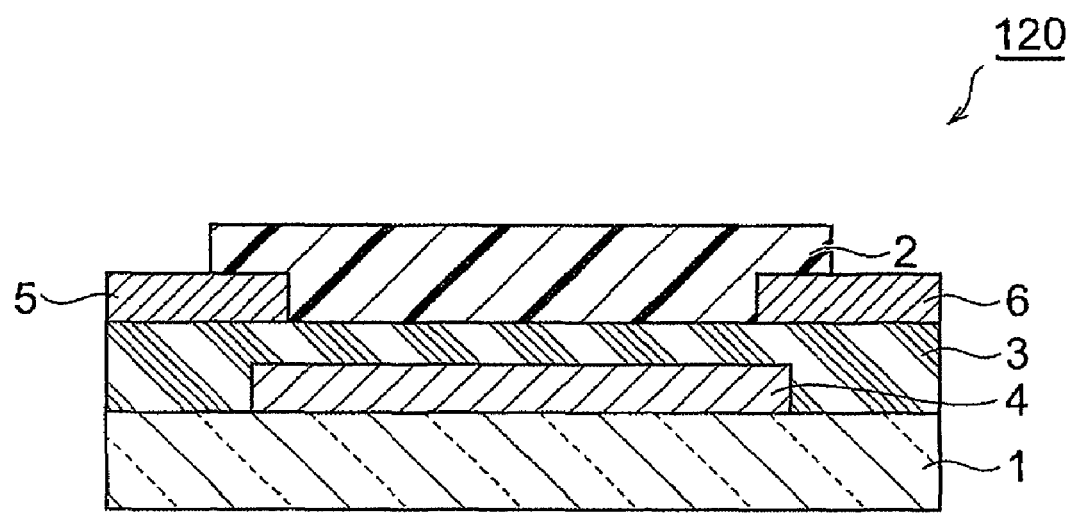
FIG. 3 is a schematic cross-sectional view of an organic thin-film transistor according to a third embodiment.

FIG. 3 is a schematic cross-sectional view of an organic thin-film transistor (field-effect organic thin-film transistor) according to a third embodiment. The organic thin-film transistor 120 shown in FIG. 3 comprises a substrate 1, a gate electrode 4 formed on the substrate 1, an insulating layer 3 formed on the substrate 1 covering the gate electrode 4, a source electrode 5 and drain electrode 6 formed at a prescribed spacing on the insulating layer 3 covering portions of the region of the insulating layer 3 under which the gate electrode 4 is formed, and an active layer 2 formed on the insulating layer 3 covering the source electrode 5 and drain electrode 6.

Figure 4:
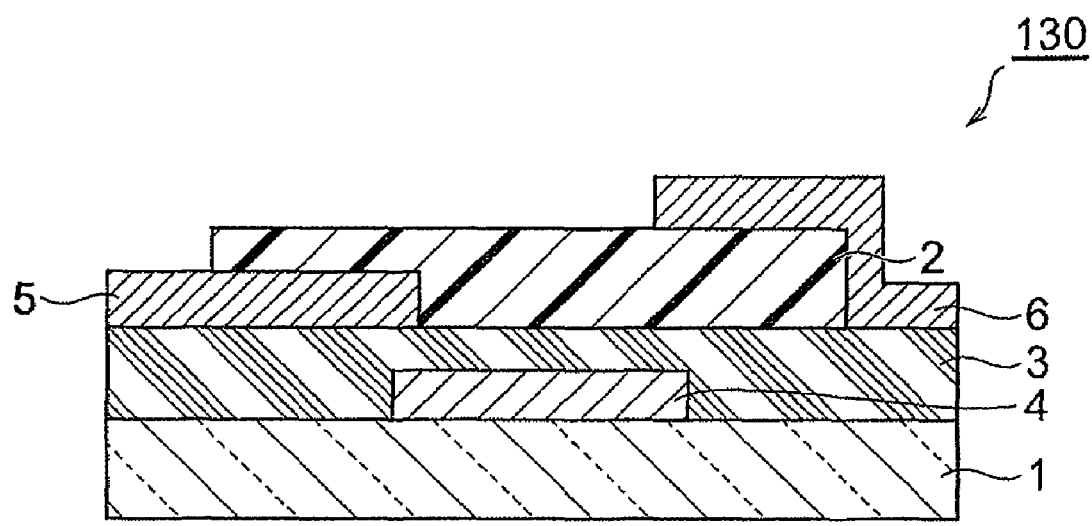
FIG. 4 is a schematic cross-sectional view of an organic thin-film transistor according to a fourth embodiment.

FIG. 4 is a schematic cross-sectional view of an organic thin-film transistor (field-effect organic thin-film transistor) according to a fourth embodiment. The organic thin-film transistor 130 shown in FIG. 4 comprises a substrate 1, a gate electrode 4 formed on the substrate 1, an insulating layer 3 formed on the substrate 1 covering the gate electrode 4, a source electrode 5 formed on the insulating layer 3 covering a portion of the region of the insulating layer 3 under which the gate electrode 4 is formed, an active layer 2 formed on the insulating layer 3 covering the source electrode 5, and a drain electrode 6 formed on the insulating layer 3 at a prescribed spacing from the source electrode 5 and covering a portion of the region of the active layer 2 under which the gate electrode 4 is formed.

Figure 12:
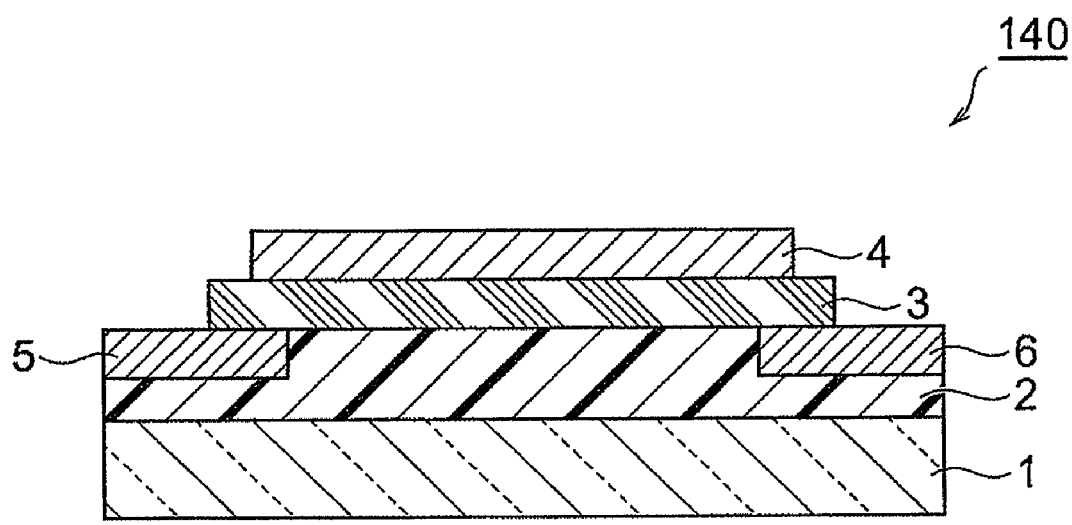
FIG. 12 is a schematic cross-sectional view of an organic thin-film transistor according to a fifth embodiment.

FIG. 12 is a schematic cross-sectional view of an organic thin-film transistor (field-effect organic thin-film transistor) according to a fifth embodiment. The organic thin-film transistor 140 shown in FIG. 12 comprises a substrate 1, an active layer 2 formed on the substrate 1, a source electrode 5 and drain electrode 6 formed at a prescribed spacing on the active layer 2, an insulating layer 3 formed on the active layer 2 covering the source electrode 5 and drain electrode 6, and a gate electrode 4 formed on the insulating layer 3, covering a portion of the region of the insulating layer 3 under which the source electrode 5 is formed and a portion of the region of the insulating layer 3 under which the drain electrode 6 is formed.

Figure 13:
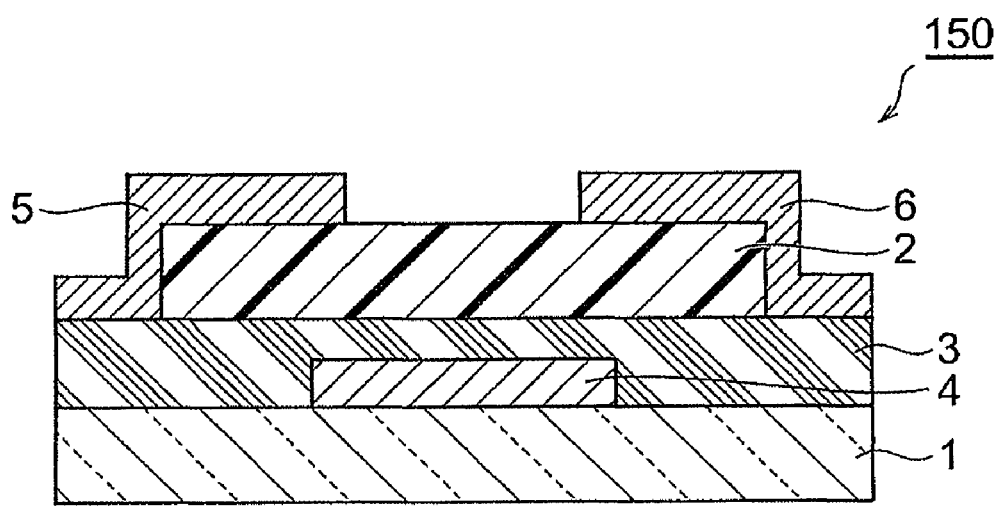
FIG. 13 is a schematic cross-sectional view of an organic thin-film transistor according to a sixth embodiment.

FIG. 13 is a schematic cross-sectional view of an organic thin-film transistor (field-effect organic thin-film transistor) according to a sixth embodiment. The organic thin-film transistor 150 shown in FIG. 13 comprises a substrate 1, a gate electrode 4 formed on the substrate 1, an insulating layer 3 formed on the substrate 1 covering the gate electrode 4, an active layer 2 formed covering the region of the insulating layer 3 under which the gate electrode 4 is formed, a source electrode 5 formed on the insulating layer 3 covering a portion of the region of the active layer 2 under which the gate electrode 4 is formed, and a drain electrode 6 formed on the insulating layer 3 at a prescribed spacing from the source electrode 5 and covering a portion of the region of the active layer 2 under which the gate electrode 4 is formed.

Figure 14:
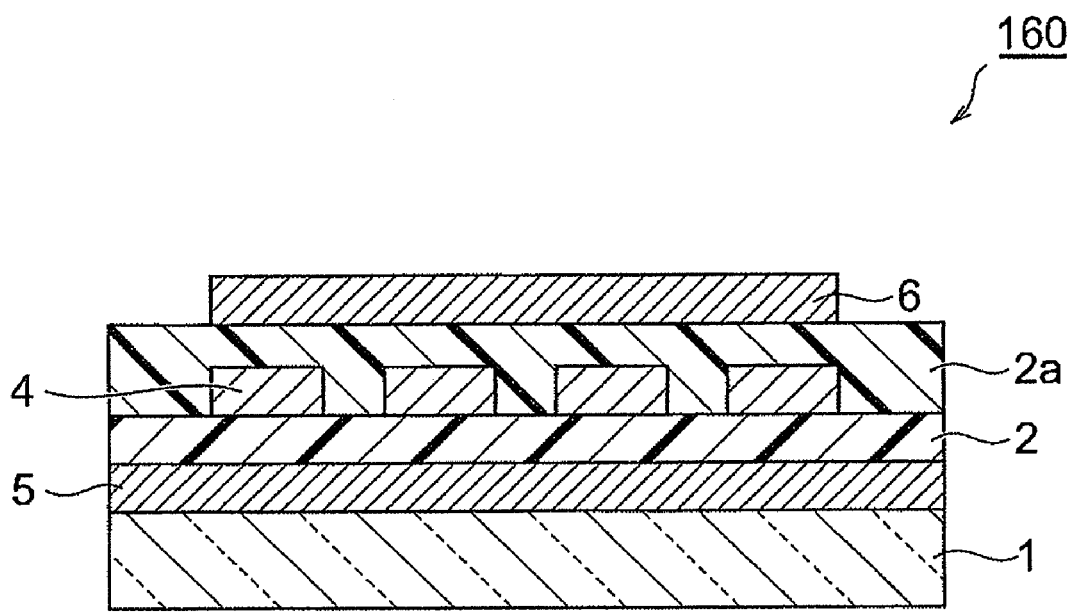
FIG. 14 is a schematic cross-sectional view of an organic thin-film transistor according to a seventh embodiment.

FIG. 14 is a schematic cross-sectional view of an organic thin-film transistor (static induction organic thin-film transistor) according to a seventh embodiment. The organic thin-film transistor 160 shown in FIG. 14 comprises a substrate 1, a source electrode 5 formed on the substrate 1, an active layer 2 formed on the source electrode 5, a plurality of gate electrodes 4 formed at prescribed spacings on the active layer 2, an active layer 2a formed on the active layer 2 covering all of the gate electrodes 4 (the material composing the active layer 2a may be the same as or different from that of the active layer 2), and a drain electrode 6 formed on the active layer 2a.

In the organic thin-film transistors of the first to seventh embodiments described above, the active layer 2 and/or the active layer 2a contains a compound and/or polymer according to the invention and forms a current channel between the source electrode 5 and drain electrode 6. The gate electrode 4 controls the level of current flowing through the current channel of the active layer 2 and/or active layer 2a by application of voltage.

This type of field-effect organic thin-film transistor can be manufactured by a publicly known process, such as the process described in Japanese Unexamined Patent Publication BET No. 5-110069, for example. The static induction organic thin-film transistor can also be manufactured by a publicly known process such as the process described in Japanese Unexamined Patent Publication No. 2004-006476, for example.

The material of the substrate 1 is not particularly restricted so long as it does not impair the characteristics of the organic thin-film transistor, and a glass panel, flexible film substrate or plastic substrate may be used.

Since organic solvent-soluble compounds are highly advantageous and preferred in forming the active layer 2, the organic thin-film production process of the invention described above may be used to form organic thin-films composed of the active layer 2.

The insulating layer 3 in contact with the active layer 2 is not particularly restricted so long as it is a material with high electrical insulating properties, and any publicly known one may be used. As examples there may be mentioned SiOx, SiNx, $Ta_2O_5$, polyimide, polyvinyl alcohol, polyvinylphenol and organic glass. From the viewpoint of lower voltage, a material with high permittivity is preferred.

When the active layer 2 is formed on the insulating layer 3, it may be formed after surface modification by treatment of the surface of the insulating layer 3 with a surface treatment agent such as a silane coupling agent in order to improve the interfacial properties between the insulating layer 3 and active layer 2. As surface treatment agents there may be mentioned long-chain alkylchlorosilanes, long-chain alkylalkoxysilanes, fluorinated alkylchlorosilanes, fluorinated alkylalkoxysilanes and silylamine compounds such as hexamethyldisilazane. Before treatment with the surface treatment agent, the insulating layer surface may be pre-treated by ozone UV or $O_2$ plasma.

After the organic thin-film transistor has been fabricated, a protecting film is preferably formed on the organic thin-film transistor to protect the device. This will help prevent reduction in the characteristics of the organic thin-film transistor when it is exposed to air. A protecting film can also minimize effects when an operating display device is formed on the organic thin-film transistor.

The method of forming the protecting film may involve covering with a UV cured resin, thermosetting resin, inorganic SiONx film or the like. For effective shielding of the organic thin-film transistor from air during formation of the protecting film, the steps after fabrication of the organic thin-film transistor and before formation of the protecting film are preferably carried out without exposure to air (for example, in a dry nitrogen atmosphere or in a vacuum).

Figure 5:
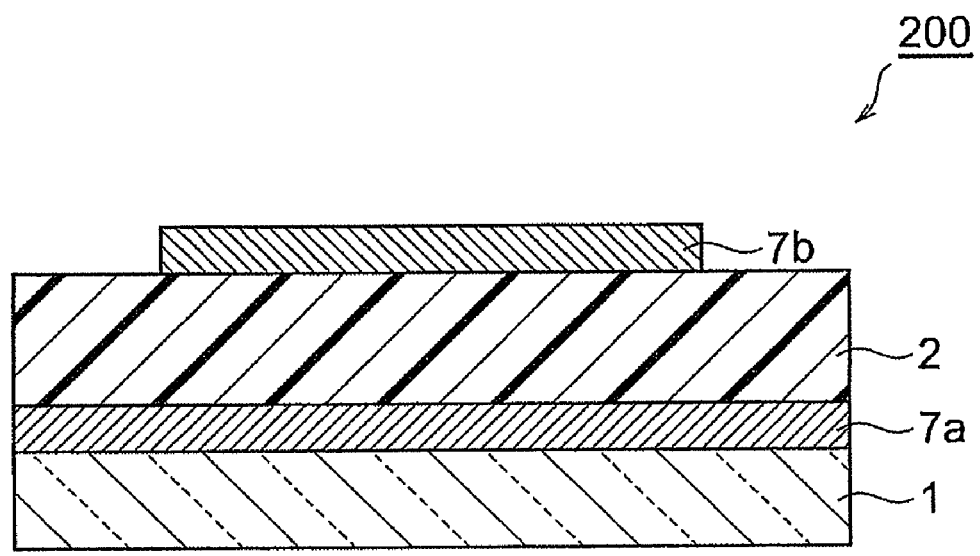
FIG. 5 is a schematic cross-sectional view of a solar cell according to an embodiment of the invention.

Application of an organic thin-film of the invention in a solar cell will now be explained. FIG. 5 is a schematic cross-sectional view of a solar cell according to an embodiment of the invention. The solar cell 200 shown in FIG. 5 comprises a substrate 1, a first electrode 7a formed on the substrate 1, an active layer 2 comprising an organic thin-film that contains a compound and/or polymer of the invention formed on the first electrode 7a, and a second electrode 7b formed on the active layer 2.

In the solar cell of this embodiment, a transparent or semi-transparent electrode is used for either to one of the first electrode 7a and second electrode 7b. As electrode materials there may be used metals such as aluminum, gold, silver, copper, alkali metal and alkaline earth metals or their semi-transparent films, or transparent conductive films. In order to obtain high open voltage, it is preferred to select the electrodes so as to produce a large work function difference. Carrier generators, sensitizing agents and the like may also be added in order to increase photosensitivity in the active layer 2 (organic thin-film). The material for the substrate 1 may be a silicon base, glass panel, plastic sheet or the like.

Figure 6:
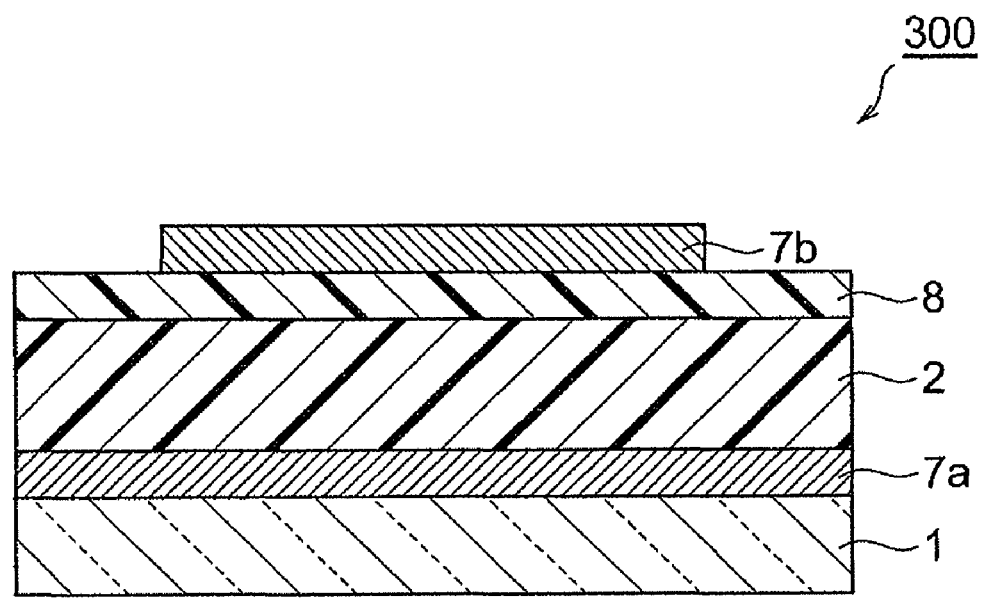
FIG. 6 is a schematic cross-sectional view of an optical sensor according to a first embodiment.

Application of an organic thin-film of the invention in an optical sensor will now be explained. FIG. 6 is a schematic cross-sectional view of an optical sensor according to a first embodiment. The optical sensor 300 shown in FIG. 6 comprises a substrate 1, a first electrode 7a formed on the substrate 1, an active layer 2 comprising an organic thin-film that contains a compound and/or polymer of the invention formed on the first electrode 7a, a charge generation layer 8 formed on the active layer 2, and a second electrode 7b formed on the charge generation layer 8.

Figure 7:
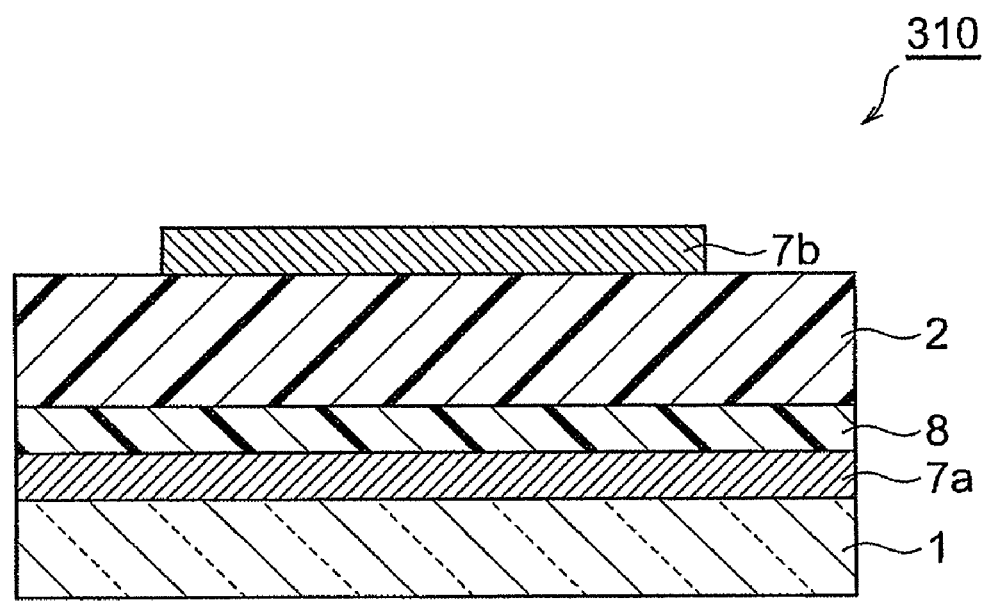
FIG. 7 is a schematic cross-sectional view of an optical sensor according to a second embodiment.

FIG. 7 is a schematic cross-sectional view of an optical sensor according to a second embodiment. The optical sensor 310 shown in FIG. 7 comprises a substrate 1, a first electrode 7a formed on the substrate 1, a charge generation layer 8 formed on the first electrode 7a, an active layer 2 comprising an organic thin-film that contains a compound and/or polymer of the invention formed on the charge generation layer 8, and a second electrode 7b formed on the active layer 2.

Figure 8:
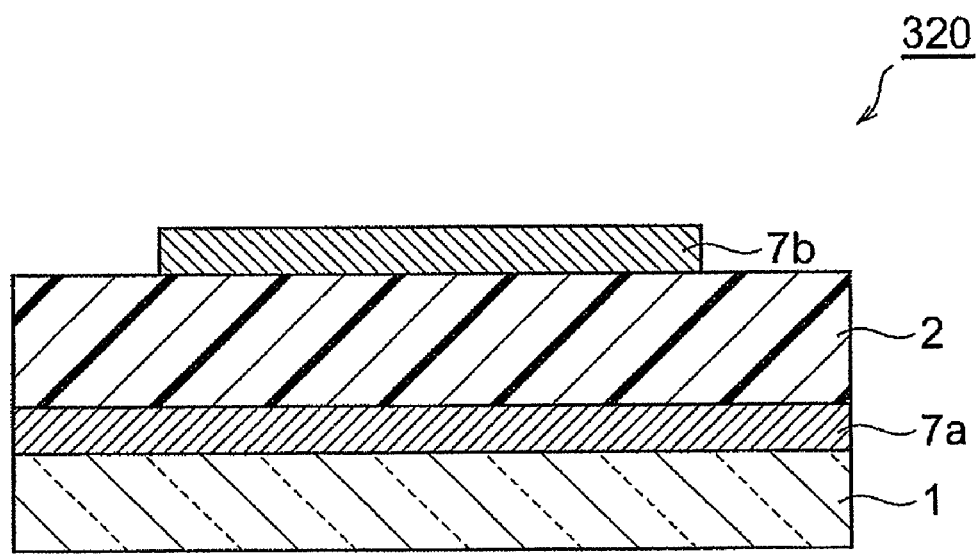
FIG. 8 is a schematic cross-sectional view of an optical sensor according to a third embodiment.

FIG. 8 is a schematic cross-sectional view of an optical sensor according to a third embodiment. The optical sensor 320 shown in FIG. 8 comprises a substrate 1, a first electrode 7a formed on the substrate 1, an active layer 2 comprising an organic thin-film that contains a compound and/or polymer of the invention formed on the first electrode 7a, and a second electrode 7b formed on the active layer 2.

In the optical sensors of the first to third embodiments, a transparent or semi-transparent electrode is used for either to one of the first electrode 7a and second electrode 7b. The charge generation layer 8 is a layer that generates an electrical charge upon absorption of light. As electrode materials there may be used metals such as aluminum, gold, silver, copper, alkali metal and alkaline earth metals or their semi-transparent films, or transparent conductive films. Carrier generators, sensitizing agents and the like may also be added in order to increase photosensitivity in the active layer 2 (organic thin-film). The material for the substrate 1 may be a silicon base, glass panel, plastic sheet or the like.

EXAMPLES

The present invention will now be explained in greater detail based on examples and comparative examples, with the understanding that the invention is in no way limited to the examples.

(Measuring Conditions)

The nuclear magnetic resonance (NMR) spectra were measured using a JMN-270 (270 MHz for $^1$H measurement) or a JMNLA-600 (600 MHz for $^{19}$F measurement), both trade names of JEOL Corp. The chemical shifts are represented as parts per million (ppm). Tetramethylsilane (TMS) was used as the internal standard (0 ppm). The coupling constant (J) is represented in Hz, and the symbols s, d, t, q, m and br respectively represent singlet, doublet, triplet, quartet, multiplet and broad. The mass spectrometry (MS) was performed using a GCMS-QP5050A, trade name of Shimadzu Corp., by electron ionization (EI) or direct inlet (DI). The silica gel used for separation by column chromatography was Silicagel 60N (40-50 μm), trade name of Kanto Kagaku Co., Ltd. All of the chemical substances were reagent grade and purchased from Wako Pure Chemical Industries, Ltd., Tokyo Kasei Kogyo Co., Ltd., Kanto Kagaku Co., Ltd., Nacalai Tesque, Inc., Sigma Aldrich Japan, KK. or Daikin Chemicals Co., Ltd. Cyclic voltammetry was performed using an apparatus by BAS Inc., with a Pt electrode by BAS Inc. as the work electrode, Pt wire as the counter electrode and Ag wire as the reference electrode. The sweep rate during measurement was 100 mV/sec, and the scanning potential range was −2.8 V to 1.6 V. The reduction potential and oxidation potential were measured after completely dissolving 1×10$^{-3}$ mol/L of the compound and 0.1 mol/L of tetrabutylammonium hexafluorophosphate (TBAPF6) as a supporting electrolyte in a monofluorobenzene solvent. X-ray structural analysis (XRD) was performed using a Rigaku RAXIS-RAPID imaging plate diffractometer.

Reference Synthesis Example 1

Synthesis of Compound (78)

The starting compound 4H-cyclopenta[2,1-b:3,4-b'] dithiophen-4-one (compound (77)) was synthesized with reference to the description in Brzezinski, J. Z., Reynolds, J. R. Synthesis 2002, 8, 1053-1056. This compound (77) was used to synthesize compound (78) below with reference to the description in Ong, B. S. Tetrahedron Lett. 1980, 21, 4225-4228. Specifically, compound (77) was used as the starting compound for dithioketalation according to reaction formula (c) below to synthesize compound (78).

(Chemical Formula 32)

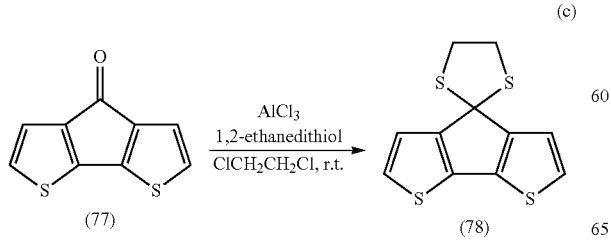

(c)

Example 1

Synthesis of Compound A

After placing N-bromosuccinimide (489 mg, 2.75 mmol) in a heat-dried two-necked flask and substituting with nitrogen, dichloromethane (4 mL) was added. The solution was cooled to −78° C., and then hydrogen fluoride-pyridine (hydrogen fluoride content: 60-70%, purchased from Sigma Aldrich Japan, KK.) (1 mL) was added dropwise. After stirring at −78° C. for 30 minutes, a dichloromethane solution (4 mL) containing 105 mg (0.39 mmol) of compound (78) was added dropwise. Stirring was continued at −78° C. for 3 hours, and then the temperature was raised to 0° C. in an ice bath prior to further stirring for 1 hour. The obtained reaction mixture was diluted with hexane at 0° C. and then passed through a basic alumina column. It was then concentrated under reduced pressure and purified by silica gel column chromatography (hexane) to obtain the target compound A (83 mg, 57% yield) as a yellow solid. The analysis results and chemical formula for the obtained compound A are shown below.

TLC R$_f$=0.6 (hexane:diethyl ether=3:1): $^1$H NMR (270 MHz, CDCl$_3$): δ 7.10 (s, 2H): GC-MS (EI): m/z=372 (M$^+$).

(Chemical Formula 33)

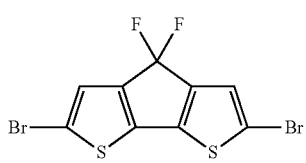

(A)

Example 2

Synthesis of Compound B

Compound A (446 mg, 1.20 mmol) and tetrahydrofuran (2.5 mL) were placed in a heat-dried volumetric flask. The mixture was then substituted with nitrogen and cooled to −78° C., after which n-butyllithium (1.6 M, 0.81 mL, 1.3 mmol) was added for reaction. After 1 hour, the temperature was raised to room temperature. Water was then added, and after extracting the organic phase with ethyl acetate, the organic phase was dried over magnesium sulfate. It was then concentrated under reduced pressure and purified by silica gel column chromatography (hexane) to obtain the target compound 3 (246 mg, 70% yield) as a green liquid. The analysis results and chemical formula for the obtained compound B are shown below.

TLC R$_f$=0.6 (hexane): GC-MS (EI): m/z=294 (M$^+$).

(Chemical Formula 34)

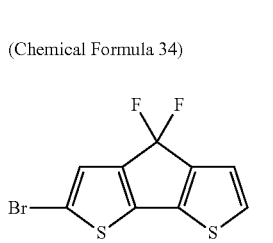

(B)

Example 3

Synthesis of compound C

Compound A (351 mg, 0.94 mmol) and tetrahydrofuran (10 mL) were placed in a heat-dried volumetric flask. The mixture was cooled to 0° C. with an ice bath, and after adding lithium aluminum hydride (219 mg, 5.77 mmol), reaction was conducted at room temperature. After 4 hours, water (220 mg), a 2N sodium hydroxide aqueous solution (220 mg) and water (660 mg) were added in that order. The obtained mixture was stirred at room temperature and filtered with Celite, and then concentrated under reduced pressure. It was then purified by silica gel column chromatography hexane) to obtain the target compound C (191 mg, 95% yield) as a white solid. The analysis results and chemical formula for the obtained compound C are shown below. Upon measuring the obtained compound C by cyclic voltammetry (CV), the oxidation potential was 0.99 V and the reduction potential was −2.42 V. The peak wavelength in the absorption spectrum of compound C was 359 nm.

TLC $R_f$=0.4 (hexane): $^1$H NMR (270 MHz, CDCl$_3$): δ 7.16 (d, 2H, J=5.0 Hz), 7.08 (d, 2H, J=5.0 Hz): GC-MS (EI): i/z=214 (M$^+$).

(Chemical Formula 35)

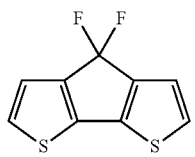

(C)

Example 4

Synthesis of Compound D

Compound C (40 mg, 0.19 mmol) and tetrahydrofuran (2.0 mL) were placed in a heat-dried volumetric flask. The mixture was then substituted with nitrogen and cooled to −78° C., after which n-butyllithium (1.6 M, 0.13 mL, 0.21 mmol) was added for reaction. After one hour, tributyltin chloride (100 mg, 0.307 mmol) was added at −78° C. and the temperature was raised to room temperature. After 12 hours, water was added and the organic phase was extracted with dichloromethane. The organic phase was dried over magnesium sulfate and concentrated under reduced pressure. It was then purified with an alumina column (hexane) to obtain the target compound D (70 mg, 75% yield) as a pale yellow liquid. The analysis results and chemical formula for the obtained compound D are shown below.

TLC $R_f$=0.6 (hexane): GC-MS (DI): m/z=504 (M$^+$).

(Chemical Formula 36)

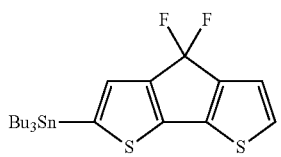

(D)

Example 5

Synthesis of Compound E

After placing compound A (125 mg, 0.336 mmol), 2-tributylstannylthiophene (423 mg, 1.13 mmol), tetrakis(triphenylphosphine)palladium(0) (51 mg, 0.0441 mmol) and toluene (3 mL) in a heat-dried stoppered test tube, it was substituted with nitrogen and reaction was conducted at 120° C. After 15 hours, it was allowed to cool, filtered with Celite and then concentrated under reduced pressure. It was then purified with an alumina column (hexane) to obtain the target compound E (71 mg, 56% yield) as a reddish-orange solid. The analysis results and chemical formula for the obtained compound E are shown below. Upon measuring the obtained compound E by CV, the oxidation potential was 0.57 V and the reduction potential was −2.03 V. The peak wavelength in the absorption spectrum of compound E was 433 nm.

TLC $R_f$=0.2 (hexane): $^1$H NMR (270 MHz, CDCl$_3$): δ 7.02 (dd, 2H, J=5.0, 3.6 Hz), 7.16 (s, 2H), 7.18 (t, 2H, J=3.6, 1.0 Hz), 7.25 (t, 21, J=5.0, 1.0 Hz): GC-MS (EI): m/z=378 (M$^+$).

(Chemical Formula 37)

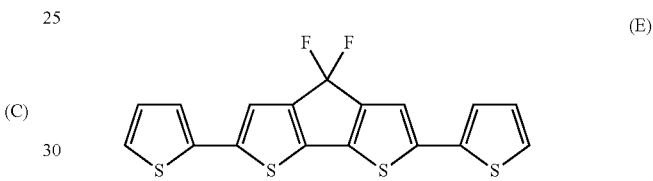

(E)

Example 6

Synthesis of Compound F

After placing compound A (130 mg, 0.349 mmol), 2-tributylstannyl-5-perfluorohexylthiophene (672 mg, 0.972 mmol), tetrakis(triphenylphosphine)palladium(0) (40 mg, 0.0346 mmol) and toluene (3 mL) in a heat-dried stoppered test tube, it was substituted with nitrogen and the mixture was circulated for 13 hours. After filtration with Celite, it was then concentrated under reduced pressure. It was then purified with an alumina column (hexane) to obtain the target compound F (131 mg, 38% yield) as an orange solid. The analysis results and chemical formula for the obtained compound F are shown below. Upon measuring the obtained compound F by CV, the oxidation potential was 0.88 V and the reduction potential was −1.95 V. The peak wavelength in the absorption spectrum of compound F was 433 nm.

TLC $R_f$=0.5 (hexane): $^1$H NMR (270 MHz, acetone-d$_6$): δ 7.66 (s, 2H, 7.65 (d, 2H, J=4.3 Hz), 7.54 (d, 2H, J=4.3 Hz): MS (MALDI-TOF, 1,8,9-trihydroxyanthracene matrix) m/z=1018.5 (M$^+$, Calcd 1014.6).

(Chemical Formula 38)

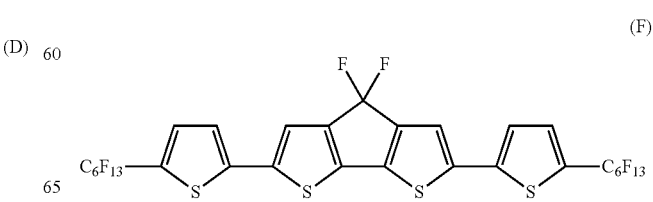

(F)

X-Ray Structural Analysis

Figure 10:
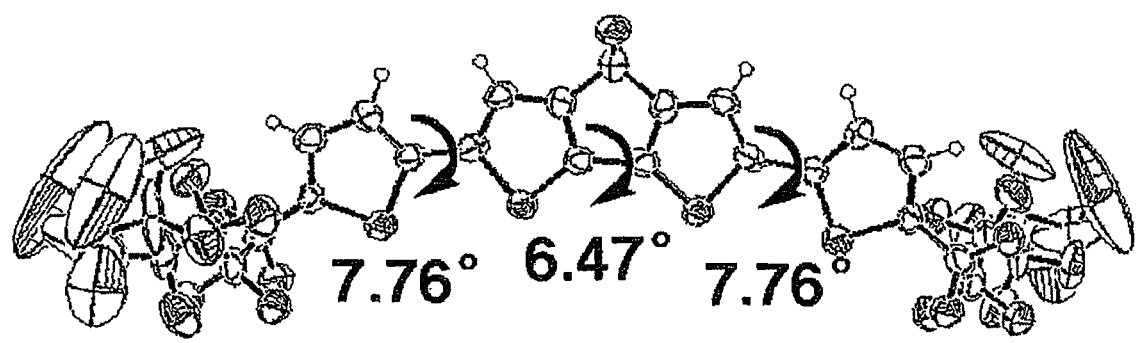
FIG. 10 is a schematic drawing of the molecular structure of compound F.
Figure 11:
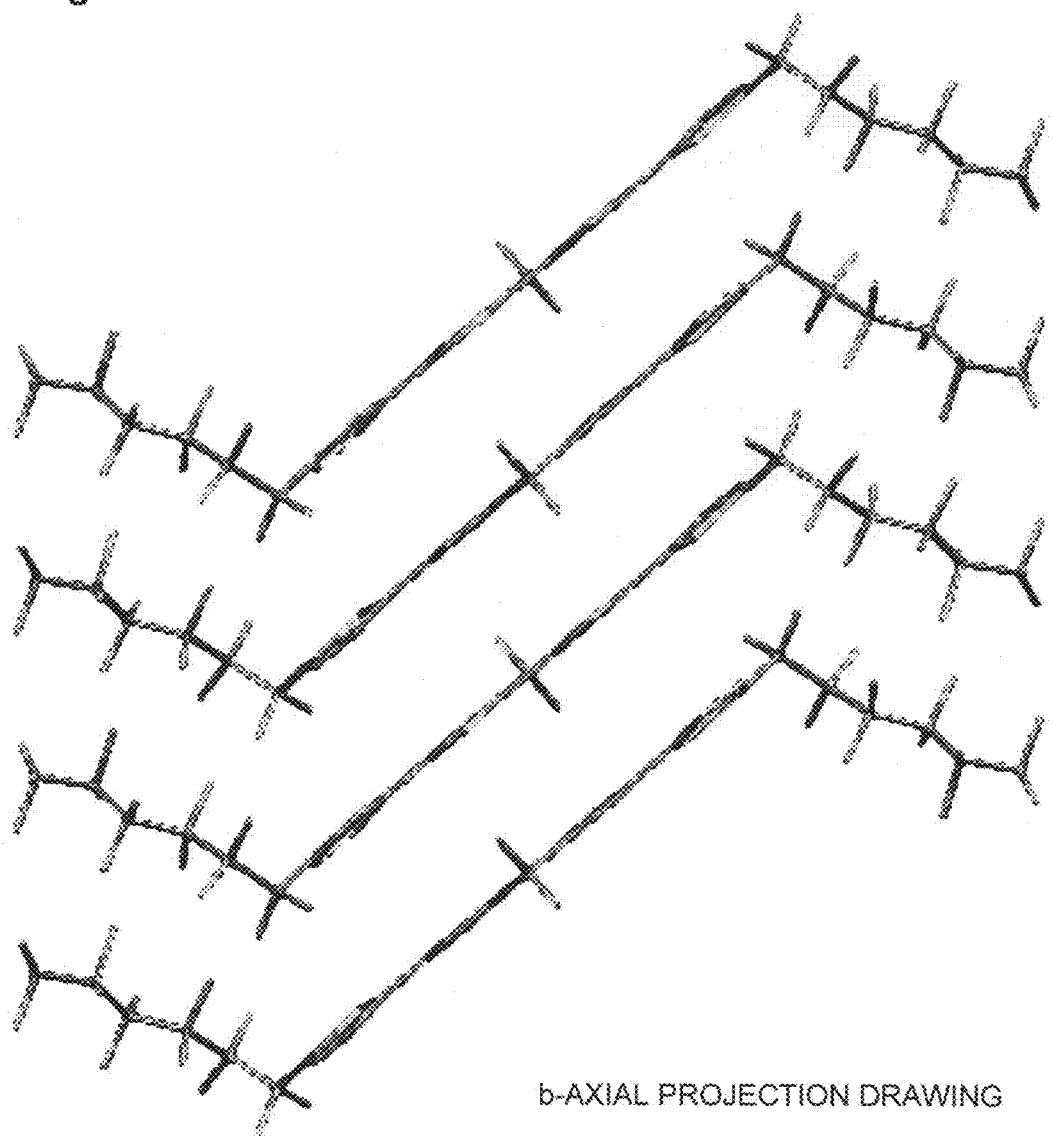
FIG. 11 is a schematic b-axial projection drawing of the structure of compound F in a crystal.

When the obtained compound F was subjected to X-ray structural analysis to measure the torsional angle between adjacent thiophene rings, the torsional angle formed between the thiophene rings of the central bithiophene portion was approximately 6 degrees and the torsional angles formed between the thiophene rings at the central bithiophene portion and the thiophene rings at both ends were approximately 8 degrees, and therefore the form was essentially planar (see FIG. 10). It was also confirmed that Compound F had a homogeneous stack structure in the crystal (see FIG. 11).

Example 7

Synthesis of Polymer G

After placing compound B (26 mg, 0.089 mmol), compound C (70 mg, 0.14 mmol), tetrakis(triphenylphosphine)palladium(0) (25 mg, 0.022 mmol) and toluene (1.8 mL) in a heat-dried stoppered test tube, it was substituted with nitrogen and reaction was conducted at 120° C. After 14 hours, it was allowed to cool, filtered with Celite and then concentrated under reduced pressure. It was then purified with an alumina column (hexane) to obtain the target polymer G (15 mg, 40% yield) as a yellowish-orange solid. The analysis results and chemical formula for the obtained polymer G are shown below. Upon measuring the obtained polymer G by CV, the oxidation potential was 0.66 V and the reduction potential was −2.08 V. The peak wavelength in the absorption spectrum of polymer G was 435 nm.

TLC $R_f$=0.4 (hexane: $CH_2Cl_2$=4:1): $^1$H NMR (270 MHz, $CDCl_3$): δ 7.22 (d, 2H, J=4.9 Hz), 7.15 (s, 2H), 7.11 (d, 2H, J=4.9 Hz): GC-MS (DI): m/z=426 ($M^+$).

(Chemical Formula 39)

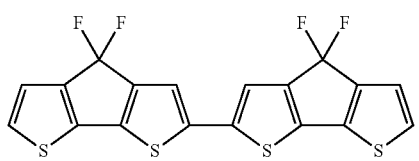

(G)

Example 8

Synthesis of Polymer H

After placing compound A (172 mg, 0.462 mmol), compound D (516 mg, 1.03 mmol), tetrakis(triphenylphosphine)palladium(0) (73 mg, 0.063 mmol) and toluene (10 mL) in a heat-dried stoppered test tube, it was substituted with nitrogen and reaction was conducted at 120° C. After 10 hours it was allowed to cool, and the precipitated solid was filtered out and washed with acetone, hexane and methanol. The washed solid was subjected to sublimation purification to obtain the target polymer H (95 mg, 42%) as a brown solid. The analysis results and chemical formula for the obtained polymer H are shown below. The peak wavelength in the absorption spectrum of polymer H was 488 nm.

GC-MS (DI): m/z 638 ($M^+$).

(Chemical Formula 40)

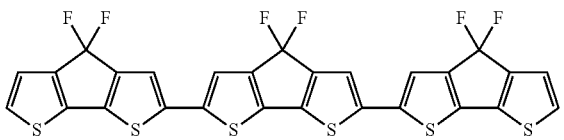

(H)

Example 9

Synthesis of Polymer J

After placing 2,7-bis(trimethylstannyl)-9,9-dioctylfluorene (0.13 mmol), compound A (0.11 mmol) and dichlorobis(triphenylphosphine)palladium (0.97 μmol) in a 50 ml nitrogen-substituted Schlenk flask, 3 ml of DMF (dimethylformamide) was added and the temperature was raised to 150° C. before stirring for 24 hours. Next, 2 ml of THF (tetrahydrofuran) was added and the mixture was stirred for 48 hours. After cooling to room temperature, reprecipitation was performed with 50 ml of a mixture of methanol and water in a weight ratio of 1:1 to obtain the target polymer J (50 mg, 77%) as a brown solid. The polystyrene-based number-average molecular weight of the obtained polymer J was $4.4×10^3$. The analysis results and chemical formula for the obtained polymer J are shown below. The peak wavelength in the absorption spectrum of polymer J in thin-film form was 364 nm.

(Chemical Formula 41)

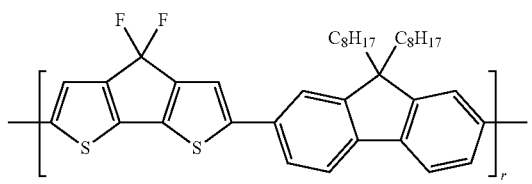

(J)

Comparative Example 1

Synthesis of Compound K

After placing compound (77) (96 mg, 0.499 mmol), hydrazine monohydrate (268 mg, 5.35 mmol), potassium hydroxide (294 mg, 5.249 mmol) and ethylene glycol (5 mL) in a heat-dried stoppered test tube, the mixture was slowly heated from room temperature to 190° C. and then refluxed at 190° C. for 13 hours. After then cooling the mixture to room temperature, water was added and the organic phase was extracted with ether. The organic phase was washed with water and brine and dried over magnesium sulfate, and concentrated under reduced pressure. It was then purified by silica gel column chromatography (hexane:ethyl acetate=10:1) to obtain the target compound K (59 mg, 66% yield) as a white solid. The analysis results and chemical formula for the obtained compound K are shown below. Upon measuring the obtained compound K by CV, the oxidation potential was 0.68 V and the reduction potential was −2.88 V. The peak wavelength in the absorption spectrum of compound K was 310 nm.

TLC $R_f$=0.7 (hexane: $CH_2Cl_2$=2:1): $^1$H NMR (270 MHz, $CDCl_3$): δ 7.17 (d, 2H, J=4.8 Hz), 7.09 (d, 2H, J=4.8 Hz), 3.54 (s, 2H): GC-MS (EI): m/z=178 ($M^+$).

(Chemical Formula 42)

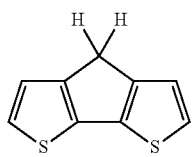

(K)

Example 10

Fabrication of Organic Thin-Film Device 1 and Evaluation of Transistor Property A substrate was prepared by forming a silicon oxide film as the insulating layer by thermal oxidation to a thickness of 300 nm on the surface of a highly doped n-type silicon wafer as the gate electrode. The substrate was immersed in hexamethyldisilazane (HMDS) by Aldrich at 50° C. for 7 hours for treatment of the silicon oxide film surface. An organic thin-film of compound F was accumulated on the surface-treated substrate to a film thickness of 15 nm by vacuum vapor deposition under conditions with a substrate temperature of 90° C. and a deposition rate of 2.0 angstrom/sec. Au was formed to a thickness of 30 nm on the organic thin-film by vapor deposition through a shadow mask, to form a source electrode and drain electrode with a channel width of 5.5 mm and a channel length of 100 μm, thus fabricating organic thin-film device 1. The transistor property of the obtained organic thin-film device 1 was measured while varying the gate voltage $V_G$ and the source-drain voltage $V_{SD}$ in a vacuum, and as a result a satisfactory Id-Vg property was confirmed and a drain current of Id=7.3×10$^{-6}$ A flowed at Vg=100 V, Vd=100 V. The mobility was 1.8×10$^{-2}$ $cm^2$/Vs, and the threshold voltage with current on was Vth=64 V. These results confirmed that the organic thin-film device 1 employing compound F effectively functions as an n-type organic transistor.

Example 11

Fabrication of Organic Thin-Film Device 2 and Evaluation of Organic Thin-Film Transistor Property Polymer J was weighed out to 0.008 g, and then 2 g of dichlorobenzene was added to prepare a coating solution. The coating solution of polymer J was coated onto a surface-treated electrode-bearing substrate by spin coating, in the same manner as Example 10. This resulted in formation of an organic thin-film comprising polymer J to a film thickness of 700 nm on the substrate, thus fabricating organic thin-film device 2. The transistor property of the obtained organic thin-film device 2 was measured while varying the gate voltage $V_G$ and the source-drain voltage $V_{SD}$ in a vacuum, and as a result a satisfactory $I_{Sd}$-Vg property was confirmed, demonstrating effective functioning as an n-type organic transistor.

Reference Synthesis Example 2

Synthesis of Compound (80)

The starting compound 2,2-di-(3-thienyl)-1,3-dioxolane (compound (79)) was synthesized with reference to the description in Lucas, P.; El Mehdi, N.; Ho, H. A.; Belanger, D.; Breau, L., Synthesis 2000, 9, 1253-1258. This compound (79) was used to synthesize compound (80) below with reference to the description in Zotti, G.; Zecchin, S.; Schiavon, G; Vercelli, B. Chem. Mater. 2004, 16, 3667-3676. Specifically, compound (79) was used as the starting compound for monobromination according to reaction formula (d) below to synthesize compound (80).

(Chemical Formula 43)

(d)

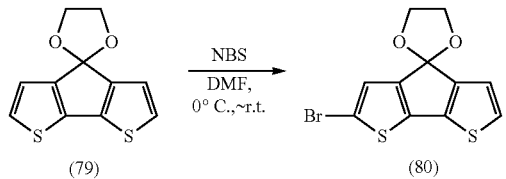

(79)    (80)

Synthesis of Compound L

After placing compound (80) (600 mg, 1.90 mmol), copper powder (777 mg, 12.2 mmol), perfluorohexane iodide (1.11 g, 2.48 mmol) and dimethyl sulfoxide (20 mL) in a heat-dried stoppered test tube, it was substituted with nitrogen and reaction was conducted at 115° C. After 12 hours, the mixture was allowed to cool, water was added and filtration was performed with Celite. The organic phase was then extracted with ethyl acetate, and the extracted organic phase was washed with water and concentrated under reduced pressure. The organic phase that had been concentrated under reduced pressure was then dissolved in tetrahydrofuran (15 mL), and then 12N hydrochloric acid (4 mL) was added and reaction was conducted at room temperature. After 10 hours, water was added and the organic phase was extracted with ethyl acetate, and then the extracted organic phase was washed with water, dried over magnesium sulfate and concentrated under reduced pressure. It was then purified by silica gel column chromatography (hexane) to obtain the target compound L (264 mg, 37% yield) as a red solid. The analysis results and chemical formula for the obtained compound L are shown below.

TLC $R_f$=0.1 (hexane): $^1$H NMR (270 MHz, $CDCl_3$): δ 7.33 (s, 1H), 7.21 (d, 1H, J=4.9 Hz), 7.07 (d, 1H, J=4.9 Hz): GC-MS (EI): m/z=510 ($M^+$).

(Chemical Formula 44)

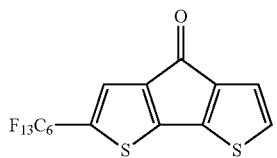

(L)

Synthesis of Compound M

After placing compound L (131 mg, 0.256 mmol), boron trifluoride-acetic acid complex (140 mg, 0.745 mmol), 1,2-ethanedithiol (66 mg, 0.701 mmol) and chloroform (4 mL) in a volumetric flask, reaction was conducted at room temperature. After 9 hours, water was added and the organic phase was extracted with dichloromethane. The organic phase was dried over magnesium sulfate and concentrated under reduced pressure. It was then purified by silica gel column chromatography (hexane:$CH_2Cl_2$=5:1) to obtain the target compound M (143 mg, 96% yield) as a light yellow solid. The analysis results and chemical formula for the obtained compound M are shown below.

TLC $R_f$=0.2 (hexane): $^1$H NMR (270 MHz, $CDCl_3$): δ 7.40 (s, 1H), 7.29 (d, 1H, J=4.9 Hz), 7.10 (d, 1H, J=4.9 Hz): GC-MS (DI): m/z=586 ($M^+$).

(Chemical Formula 45)

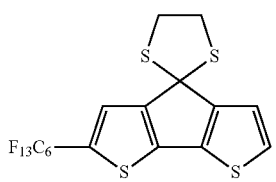

(M)

Example 12

Synthesis of Compound N

After placing N-bromosuccinimide (793 mg, 4.46 mmol) in a heat-dried two-necked flask and substituting with nitrogen, dichloromethane (10 mL) was added. The reaction mixture was cooled to −78° C., and then hydrogen fluoride-pyridine (hydrogen fluoride content: 60-70%, purchased from Sigma Aldrich Japan, KK.) (2.4 mL) was added dropwise. After stirring at −78° C. for 30 minutes, a dichloromethane solution (10 mL) containing compound M (579 mg, 0.987 mmol) was added dropwise. Stirring was continued at −78° C. for 5 hours, and then the temperature was raised to 0° C. in an ice bath prior to further stirring for 1 hour. The obtained reaction mixture was diluted with hexane at 0° C. and then passed through a basic alumina column. It was then concentrated under reduced pressure and purified by silica gel column chromatography (hexane) to obtain the target compound N (223 mg, 37% yield) as a yellow solid. The analysis results and chemical formula for the obtained compound N are shown below.

TLC $R_f$=0.8 (hexane): $^1$H NMR (270 MHz, $CDCl_3$): δ 7.41 (s, 1H), 7.16 (s, 1H): GC-MS (EI): m/z=611 ($M^+$).

(Chemical Formula 46)

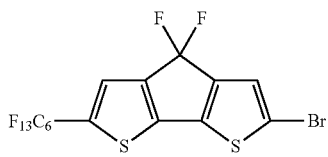

(N)

Example 13

Synthesis of Compound O

After placing compound B (129 mg, 0.448 mmol), copper powder (152 mg, 2.39 mmol), perfluorohexane iodide (490 mg, 1.10 mmol) and DMSO (3 mL) in a heat-dried stoppered test tube, it was substituted with nitrogen and reaction was conducted at 125° C. After 11 hours, the mixture was allowed to cool, water was added and filtration was performed with Celite, and then the organic phase was extracted with ethyl acetate and the extracted organic phase was washed with water, dried over magnesium sulfate and concentrated under reduced pressure. It was then concentrated under reduced pressure and purified by silica gel column chromatography hexane) to obtain the target compound O (168 mg, 61% yield) as a yellow solid. The analysis results and chemical formula for the obtained compound O are shown below.

TLC $R_f$=0.5 (hexane): $^1$H NMR (270 MHz, $CDCl_3$): δ 7.42 (s, 1H), 7.32 (d, 1H, J=5.0 Hz), 7.14 (d, 1H, J=5.0 Hz): GC-MS (EI): m/z=532 ($M^+$).

(Chemical Formula 47)

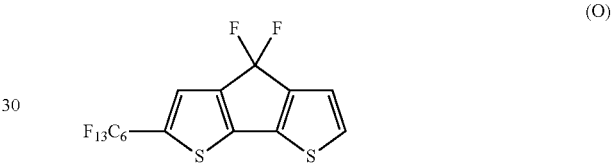

(O)

Example 14

Synthesis of Compound P

Compound O (182 mg, 0.342 mmol) and tetrahydrofuran (4 mL) were placed in a heat-dried volumetric flask. The mixture was then substituted with nitrogen and cooled to −78° C., after which n-butyllithium (1.6 M, 0.44 mL, 0.70 mmol) was added for reaction. After one hour, tributyltin chloride (222 mg, 0.68 mmol) was added at −78° C. and the temperature was raised to room temperature. After 30 minutes, water was added and the organic phase was extracted with ethyl acetate. The organic phase was dried over magnesium sulfate and concentrated under reduced pressure. It was then purified with an alumina column (hexane) to obtain the target compound P (204 mg, 34% yield) as a yellowish-brown solid. The analysis results and chemical formula for the obtained compound P are shown below.

TLC $R_f$=0.9 (hexane): $^1$H NMR (270 MHz, $CDCl_3$): δ 7.39 (s, 1H), 7.13 (s, 1H), 1.58 (m), 1.36 (m), 1.15 (m), 0.91 (m): GC-MS (DI): m/z=821 (W).

(Chemical Formula 48)

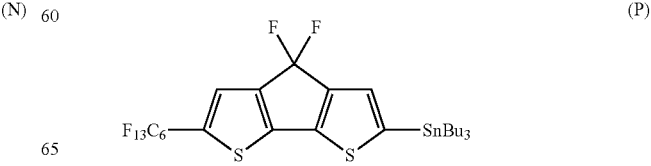

(P)

Example 15

Synthesis of Compound Q

After placing compound O (117 mg, 0.220 mmol), [bis(trifluoroacetoxy)iodo]benzene (138 mg, 0.321 mmol), iodine (56 mg, 0.221 mmol) and carbon tetrachloride (4 mL) in a volumetric flask, reaction was conducted at room temperature. After 12 hours, 1N aqueous sodium thiosulfate (10 mL) was added and the organic phase was extracted with dichloromethane. The organic phase was dried over magnesium sulfate and concentrated under reduced pressure. It was then purified by silica gel column chromatography (hexane) to obtain the target compound Q (34 mg, 24% yield) as a light yellow solid. The analysis results and chemical formula for the obtained compound Q are shown below.

TLC $R_f$=0.6 (hexane): $^1$H NMR (270 MHz, CDCl$_3$): δ 7.41 (s, 1H), 7.32 (s, 1H): GC-MS (DI): m/z=658 (M$^+$).

(Chemical Formula 49)

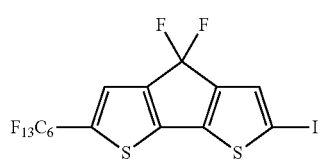

(Q)

Example 16

Synthesis of Compound R

Compound A (279 mg, 0.75 mmol) and tetrahydrofuran (8.0 mL) were placed in a heat-dried volumetric flask. The mixture was then substituted with nitrogen and cooled to −78° C., after which n-butyllithium (1.6 M, 0.6 mL, 0.96 mmol) was added for reaction. After 2 hours, tributyltin chloride (271 mg, 0.83 mmol) was added at −78° C. and the temperature was raised to room temperature. After one hour, water was added and the organic phase was extracted with dichloromethane. The organic phase was dried over magnesium sulfate and concentrated under reduced pressure. It was then purified with an alumina column (hexane) to obtain the target compound R (204 mg, 34% yield) as a yellowish-brown liquid. The analysis results and chemical formula for the obtained compound R are shown below.

TLC $R_f$=0.8 (hexane): $^1$H NMR (270 MHz, CDCl$_3$): δ 7.06 (s, 2H), 1.56 (m), 1.34 (m), 1.13 (m), 0.90 (m): GC-MS (DI): m/z=792 (M$^+$).

(Chemical Formula 50)

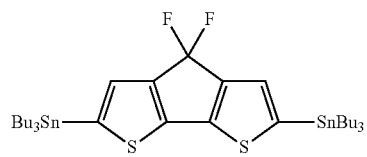

(R)

Example 17

Synthesis of Polymer S

After placing compound P (69 mg, 0.084 mmol), compound Q (30 mg, 0.046 mmol), tetrakis(triphenylphosphine)palladium(0) (5 mg, 0.006 mmol) and toluene (4 mL) in a heat-dried stoppered test tube, it was substituted with nitrogen and the mixture was circulated for 36 hours. After filtration with Celite, concentration was performed under reduced pressure. It was then purified with an alumina column (hexane) to obtain the target polymer S (44 mg, 91% yield) as a reddish-orange solid. The analysis results and chemical formula for the obtained polymer S are shown below. Upon measuring the obtained polymer S by CV, the oxidation potential was 0.98 V and the reduction potential was −1.80 V. The peak wavelength in the absorption spectrum of polymer S was 443 nm.

TLC $R_f$=0.3 (hexane): $^1$H NMR (270 MHz, THF-d$_8$): δ 7.58 (s, 2H), 7.35 (s, 2H): MS (MALDI-TOF, 1,8,9-trihydroxyanthracene matrix) m/z=1066.24 (M$^+$, Calcd 1062.56).

(Chemical Formula 51)

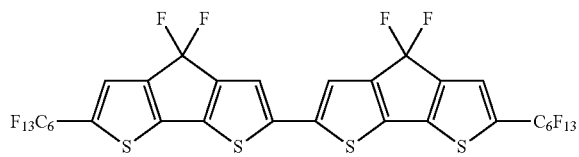

(S)

Example 18

Synthesis of Polymer T

After placing compound R (140 mg, 0.177 mmol), compound N (252 mg, 0.412 mmol), tetrakis(triphenylphosphine)palladium(0) (46 mg, 0.040 mmol) and toluene (10 mL) in a heat-dried stoppered test tube, it was substituted with nitrogen and reaction was conducted at 120° C. After 16 hours it was allowed to cool, and the precipitated solid was filtered out and washed with acetone, hexane and methanol. The washed solid was subjected to sublimation purification to obtain the target polymer T (95 mg, 42% yield) as a brown solid. The analysis results and chemical formula for the obtained polymer T are shown below. The peak wavelength in the absorption spectrum of polymer T was 491 nm.

MS (MALDI-TOF, 1,8,9-trihydroxyanthracene matrix) m/z=1283.24 (M$^+$, Calcd 1274.8).

(Chemical Formula 52)

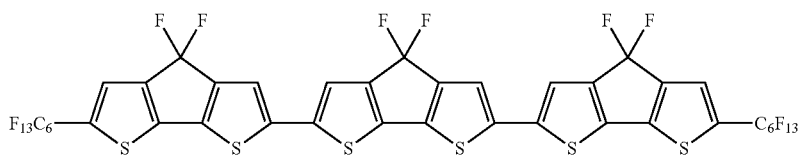

(T)

Example 19

Synthesis of Compound U

After placing compound A (38 mg, 0.10 mmol), 5-perfluorohexyl-5'-tributylstannylbithiophene (275 mg, 0.356 mmol), tetrakis(triphenylphosphine)palladium(0) (12 mg, 0.010 mmol) and toluene (3.5 mL) in a heat-dried stoppered test tube, it was substituted with nitrogen and reaction was conducted at 120° C. After 33 hours it was allowed to cool, and the precipitated solid was filtered out and washed with acetone, hexane and methanol. The washed solid was purified by HPLC (THF) to obtain the target compound U (14 mg, 7% yield) as a brown solid. The analysis results and chemical formula for the obtained compound U are shown below. Upon measuring the obtained compound U by CV, the oxidation potential was 0.56 V and the reduction potential was −1.91 V. The peak wavelength in the absorption spectrum of compound U was 475 nm.

MS (MALDI-TOF, 1,8,9-trihydroxyanthracene matrix) m/z=1181.95 (M$^+$, Calcd 1178.82).

(Chemical Formula 53)

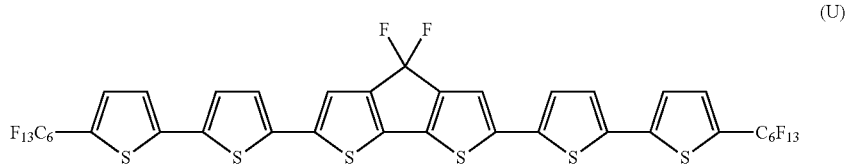

(U)

Example 20

Fabrication of Organic Thin-Film Device 3 and Evaluation of Transistor Property An organic thin-film of compound S was accumulated on a surface-treated electrode-bearing substrate to a film thickness of 15 nm by vacuum vapor deposition in the same manner as Example 10, under conditions with a substrate temperature of 90° C. and a deposition rate of 2.0 angstrom/sec. Au was formed to a thickness of 30 nm on the organic thin-film by vapor deposition through a shadow mask, to form a source electrode and drain electrode with a channel width of 5.5 mm and a channel length of 100 μm, thus fabricating organic thin-film device 3. The transistor property of the obtained organic thin-film device 3 was measured while varying the gate voltage $V_G$ and the source-drain voltage $V_{SD}$ in a vacuum, and as a result a satisfactory Id-Vg property was confirmed and a drain current of Id=5.0×10$^{-4}$ A flowed at Vg=80 V, Vd=100 V. The mobility was 1.44×10$^{-3}$ cm$^2$/Vs, and the threshold voltage with current on was Vth=53 V. These results confirmed that the organic thin-film device 3 employing compound S effectively functions as an n-type organic transistor.

The oxidation potentials and reduction potentials of the compounds and polymers obtained in Examples 3, 5-7, 17 and 19 and Comparative Example 1, as measured by CV, are shown together in Table 1.

TABLE 1

|  | Target compound | Number of thiophene rings | Oxidation potential (V) | Reduction potential (V) | Absorption peak wavelength (nm) |
| --- | --- | --- | --- | --- | --- |
| Example 3 | Compound C | 2 | 0.99 | −2.42 | 359 |
| Example 5 | Compound E | 4 | 0.57 | −2.03 | 433 |
| Example 6 | Compound F | 4 | 0.88 | −1.95 | 433 |
| Example 7 | Polymer G | 4 | 0.66 | −2.08 | 435 |
| Example 17 | Polymer S | 4 | 0.98 | −1.80 | 443 |
| Example 19 | Compound U | 6 | 0.56 | −1.91 | 475 |
| Comp. Ex. 1 | Compound K | 2 | 0.68 | −2.88 | 310 |

As clearly seen by the results in Table 1, the fluorinated compounds and fluorinated polymers of the invention were confirmed to have satisfactorily low absolute values for the reduction potential. Moreover, since a greater number of thiophene rings shifts the peak wavelength in the absorption spectrum toward the long wavelength end, improvement in the intramolecular twist and widening of intramolecular π conjugation were confirmed. It was therefore demonstrated that fluorinated compounds and fluorinated polymers according to the invention have satisfactory electron transport properties and are highly useful as organic n-type semiconductors.

Industrial Applicability

As explained above, the present invention can provide novel fluorinated compounds and novel fluorinated polymers that can be used as organic n-type semiconductors with excellent electron transport properties. Also according to the invention, it is possible to provide organic thin-films comprising the fluorinated compounds and/or fluorinated polymers, as well as organic thin-film devices comprising the organic thin-films.

The invention claimed is:

1. A fluorinated compound represented by the following general formula (II):

(Chemical Formula 2)

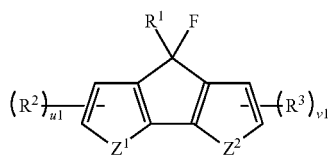

(II)

in formula (II), $R^1$ represents hydrogen or a monovalent substituent, $R^2$ and $R^3$ each independently represent a monovalent substituent, $Z^1$ and $Z^2$ each independently represent any group represented by the following formulas (i)-(viii), and u1 and v1 each independently represent an integer of 0-2; when u1 is 2, the multiple $R^2$ groups may be the same or different, and when v1 is 2 the multiple $R^3$ groups may be the same or different; $R^4$ and $R^5$ each independently represent hydrogen or a monovalent substituent; the group represented by the following formula (viii) may be left-right inverted:

(Chemical Formula 3)

(i)

(ii)

(iii)

(iv)

(v)

-continued

(vi)

(vii)

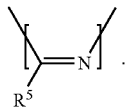

(viii)

2. A fluorinated compound according to claim 1, wherein $Z^1$ and $Z^2$ are groups represented by formula (i).

3. A fluorinated compound according to claim 1, wherein $R^1$ is a fluorine atom.

4. A process for production of a fluorinated compound according to claim 1, the process comprising a step of reacting a compound represented by the following general formula (VII) with a fluoride ion source in the presence of a halonium ion generator:

(Chemical Formula 10)

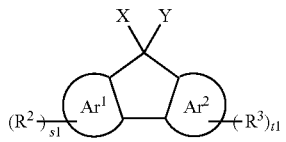

(VII)

in formula (VII), $Ar^1$ and $Ar^2$ each independently represent a $C_4$ or greater heterocyclic group, $R^2$ and $R^3$ each independently represent a monovalent substituent, X and Y each independently represent an alkylthio group, or the alkyl portions of the alkylthio groups X and Y are linked to form an alkylenedithio group, or X and Y together represent a thiocarbonyl group formed with the carbon atoms to which they are bonded, and s1 and t1 each independently represent an integer of 0 or greater; when s1 is 2 or greater, the multiple $R^2$ groups may be the same or different, and when t1 is 2 or greater the multiple $R^3$ groups may be the same or different.

5. A process for production of a fluorinated compound according to claim 4, wherein the fluoride ion source contains at least one compound selected from the group consisting of hydrogen fluoride, complexes of hydrogen fluoride and amines, complexes of hydrogen fluoride and pyridine, quaternary ammonium dihydrogen trifluorides and quaternary phosphonium dihydrogen trifluorides.

6. A process for production of a fluorinated compound according to claim 4, wherein the halonium ion generator contains at least one compound selected from the group consisting of 1,3-dibromo-5,5-dimethylhydantoin, N-bromosuccinic acid imide, N-bromoacetamide, 2,4,4,6-tetrabromo-2,5-cyclohexadienone and N-iodosuccinic acid imide.

7. A fluorinated polymer having a repeating unit represented by the following general formula (IV):

(Chemical Formula 5)

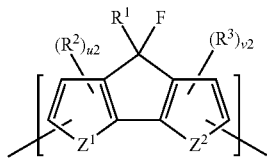
(IV)

in formula (IV), $R^1$ represents hydrogen or a monovalent substituent, $R^2$ and $R^3$ each independently represent a monovalent substituent, $Z^1$ and $Z^2$ each independently represent any group represented by the following formulas (i)-(viii), and u2 and v2 each independently represent an integer of 0 or 1; $R^4$ and $R^5$ each independently represent hydrogen or a monovalent substituent; the group represented by the following formula (viii) may be left-right inverted:

(Chemical Formula 6)

 (i)

 (ii)

 (iii)

 (iv)

 (v)

 (vi)

 (vii)

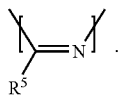 (viii)

8. A fluorinated polymer according to claim 7, wherein $Z^1$ and $Z^2$ are groups represented by formula (i).

9. A fluorinated polymer according to claim 7 which comprises at least one repeating unit represented by general formula (III) and at least one repeating unit represented by the following general formula (V):

(Chemical Formula 7)

 (V)

in formula (V), $Ar^3$ represents an optionally substituted divalent aromatic hydrocarbon or an optionally substituted divalent heterocyclic group.

10. A fluorinated polymer according to claim 9, wherein $Ar^3$ is a group represented by the following general formula (VI):

(Chemical Formula 8)

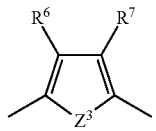 (VI)

in formula (VI), $R^6$ and $R^7$ each independently hydrogen or a monovalent substituent, and $Z^3$ represents any group represented by the following formulas (i)-(ix); $R^6$ and $R^7$ may bond together to form a ring; $R^4$, $R^5$, $R^8$ and $R^9$ each independently represent hydrogen or a monovalent substituent, and $R^8$ and $R^9$ may bond together to form a ring; the group represented by the following formula (viii) may also be left-right inverted:

(Chemical Formula 9)

 (i)

 (ii)

 (iii)

 (iv)

 (v)

 (vi)

 (vii)

 (viii)

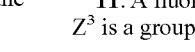 (ix)

11. A fluorinated polymer according to claim 10, wherein $Z^3$ is a group represented by formula (i).

12. A fluorinated polymer according to claim 7, wherein $R^1$ is a fluorine atom.

13. An organic thin-film comprising a fluorinated compound represented by the following general formula (II):

(Chemical Formula 2)

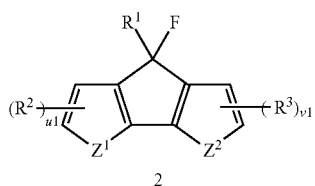

(II)

in formula (II), $R^1$ represents hydrogen or a monovalent substituent, $R^2$ and $R^3$ each independently represent a monovalent substituent, $Z^1$ and $Z^2$ each independently represent any group represented by the following formulas (i)-(viii), and u1 and v1 each independently represent an integer of 0-2; when u1 is 2, the multiple $R^2$ groups may be the same or different, and when v1 is 2 the multiple $R^3$ groups may be the same or different; $R^4$ and $R^5$ each independently represent hydrogen or a monovalent substituent; the group represented by the following formula (viii) may be left-right inverted, and/or a fluorinated polymer having a repeating unit represented by the following general formula (VII):

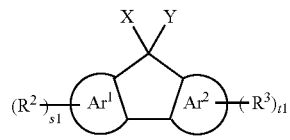

(VII)

in formula (VII), $Ar^1$ and $Ar^2$ each independently represent a $C_4$ or greater heterocyclic group, $R^2$ and $R^3$ each independently represent a monovalent substituent, X and Y each independently represent an alkylthio group, or the alkyl portions of the alkylthio groups X and Y are linked to form an alkylenedithio group, or X and Y together represent a thiocarbonyl group formed with the carbon atoms to which they are bonded, and s1 and t1 each independently represent an integer of 0 or greater; when s1 is 2 or greater, the multiple $R^2$ groups may be the same or different, and when t1 is 2 or greater the multiple $R^3$ groups may be the same or different.

14. An organic thin-film according to claim 13, which is formed by vacuum vapor deposition, spin coating, ink jet printing, dispenser printing or flexographic printing.

15. An organic thin-film device comprising an organic thin-film according to claim 13.

16. An organic thin-film transistor comprising an organic thin-film according to claim 13.

17. An organic solar cell comprising an organic thin-film according to claim 13.

* * * * *